US008808638B2

(12) United States Patent  (10) Patent No.: US 8,808,638 B2
Tomoda et al.  (45) Date of Patent: Aug. 19, 2014

(54) RETORT STERILIZATION DEVICE, HEATING DEVICE, HEAT STERILIZATION METHOD, AND HEAT TREATMENT METHOD

(75) Inventors: Hiroshi Tomoda, Sakaiminato (JP); Norio Kadowaki, Yasugi (JP); Hironobu Tomoda, Sakaiminato (JP); Manabu Moriwaki, Sakaiminato (JP); Satoru Kadowaki, Yasugi (JP)

(73) Assignees: Tomoda Selling & Sailing Co., Ltd., Tottori (JP); Tomoda Fisheries Co., Ltd., Tottori (JP); Houshou Co., Ltd, Tottori (JP); Wakisangyou Yugenkaisha, Shimane (JP)

( * ) Notice: Subject to any disclaimer, the term of this patent is extended or adjusted under 35 U.S.C. 154(b) by 40 days.

(21) Appl. No.: 13/614,290

(22) Filed: Sep. 13, 2012

(65) Prior Publication Data

US 2013/0071546 A1  Mar. 21, 2013

(30) Foreign Application Priority Data

Sep. 16, 2011 (JP) ................. 2011-203092
Jun. 12, 2012 (JP) ................. 2012-133245
Jun. 12, 2012 (JP) ................. 2012-133246

(51) Int. Cl.
*A61L 2/00* (2006.01)
*A01J 11/00* (2006.01)
*F01B 31/08* (2006.01)
*A61H 33/06* (2006.01)
*F25B 21/02* (2006.01)
*F25B 7/00* (2006.01)
*A61L 2/07* (2006.01)
*A23L 3/00* (2006.01)

(52) U.S. Cl.
CPC ... *A61L 2/00* (2013.01); *A61L 2/07* (2013.01); *A23L 3/00* (2013.01)
USPC ........... 422/298; 422/295; 422/299; 422/306; 422/307; 99/452; 99/485; 92/144; 92/186; 392/394; 62/62; 62/3.7; 62/79; 62/96; 62/513

(58) Field of Classification Search
CPC ......... A61L 2202/11; A61L 2/00; A61L 2/07; A61L 3/00
USPC ................... 422/26, 295, 298–299, 306–307; 99/452, 485; 92/144, 186; 392/394; 62/3.7, 79, 96, 185, 434, 513, 903
See application file for complete search history.

(56) References Cited

U.S. PATENT DOCUMENTS 4,057,391 A * 11/1977 Yamaguchi ..................... 422/25
5,840,248 A * 11/1998 Ongaro ............................ 422/26
2009/0311131 A1   12/2009 Tago et al.

FOREIGN PATENT DOCUMENTS

JP  10-113155   5/1998
JP  2000-220801  8/2000
(Continued)

OTHER PUBLICATIONS

Japanese Office Action and English translation thereof dated Sep. 18, 2012.

(Continued)

*Primary Examiner* — Monzer R Chorbaji
(74) *Attorney, Agent, or Firm* — Harness, Dickey & Pierce, P.L.C.

(57) ABSTRACT

A retort sterilization device includes a water steam generation device for generating water steam and a heating pot, connected to the water steam generation device, for accommodating retort food. The water steam generation device includes a heat exchanger for performing heat exchange between liquid flowing in a liquid path and heating vapor flowing in the vapor path. A top end of the liquid path of the heat exchanger is connected via a water steam supply pipe to a water steam ejection section located in an internal area of the heating pot. The heat exchanger is connected to a liquid container. A bottom end of the liquid path of the heat exchanger is connected to the liquid container via a communicating tube. The liquid container is coupled to the heating pot.

24 Claims, 15 Drawing Sheets

(56) References Cited

FOREIGN PATENT DOCUMENTS

| | | |
|---|---|---|
| JP | 2002-345446 | 12/2002 |
| JP | 2004-236991 | 8/2004 |
| JP | 2005237215 A | 9/2005 |
| JP | 2008301739 A | 12/2008 |
| JP | 4427090 B1 | 3/2010 |
| JP | 4620732 B2 | 1/2011 |
| WO | WO 2006/137418 | 12/2006 |
| WO | WO-2006137418 A1 | 12/2006 |

OTHER PUBLICATIONS

Canned, Bottled, Retort Foods Dictionary, Dec. 1, 1985, p. 148-149.

* cited by examiner

RETORT STERILIZATION DEVICE, HEATING DEVICE, HEAT STERILIZATION METHOD, AND HEAT TREATMENT METHOD

BACKGROUND OF THE INVENTION

1. Field of the Invention

The present invention relates to a retort sterilization device, a heating device, a heat sterilization method and a heat treatment method, and specifically, to a retort sterilization device including a heating pot for performing sterilization with heating and pressurization.

The present application claims the benefit of priority based upon Japanese Patent Application No. 2011-203092 filed on Sep. 16, 2011, Japanese Patent Application No. 2012-133245 filed on Jun. 12, 2012, and Japanese Patent Application No. 2012-133246 filed on Jun. 12, 2012. The entirety of the contents of these applications is incorporated herein by reference.

2. Description of the Related Art

In general, a surface or inside of food has microorganisms such as mold, yeast, bacteria and the like attached or mixed thereto. When the food contains much moisture, such microorganisms make the food rotten. As a food preservation method for avoiding this, drying, salt preservation, low-temperature preservation and the like have been performed from old days. Packaging in film makes it easy to completely block microorganisms. Thus, heat sterilization after packaging is widely used as an effective preservation method.

Heat sterilization is available in dry sterilization, which is performed with heated air, and wet sterilization, which is performed with vapor or hydroheat. Wet sterilization provides a higher sterilization effect because of the amount of heat. A simplest method of sterilization against microorganisms using wet heat is boil sterilization (sterilization in hot water), by which packaged food is put into hot water for sterilization. However, boil sterilization has the following defects. When the heating time is long, the food is deteriorated by heat; and when there is a heat-resistant microorganism which does not die even at 100° C., complete sterilization is impossible under normal pressure.

Thus, when necessary, sterilization with pressurization and heating (retort sterilization) at a temperature exceeding 100° C. is performed. When being warmed in hot water, the food cannot be heated to a temperature higher than the boiling point of water (100° C.). However, when vapor or pressurized hydroheat is used, the food can be heated to a temperature higher than 100° C. Such a method of sterilization is retort sterilization. When the food is heated at a temperature higher than 100° C., the bag packaging the food is burst during cooling because the internal pressure of the bag becomes too high. Therefore, during the cooling, the food needs to be pressurized at a pressure higher than the pressure used for heating and the pressure needs to be adjusted. In order to perform retort sterilization, a device capable of adjusting the temperature, time and pressure precisely is needed. The initial cost is higher beyond comparison than that when a boil sterilization device is used.

For performing retort sterilization on food sealed in a bag of a heat-resistant resin film or the like, the packaging bag is heated with vapor or hydroheat in a retort pot. However, it is difficult to uniformize the heating temperature in the retort pot, and thus the heating temperature may become non-uniform. Japanese Laid-Open Patent Publication No. 2008-301739 discloses a sterilization method, by which sterilization of retort food and cooling after that are performed while the food is slid in a forward-backward direction and in a leftward-rightward direction.

FIG. 16 shows a sterilization device 1000 disclosed in Japanese Laid-Open Patent Publication No. 2008-301739. In the sterilization device 1000 shown in FIG. 16, a rail 220 is provided in a retort pot main body 210, and a movable table 240 is supported by the rail 220 via wheels 230. On the movable table 240, trays 260 having many bags of retort food 250 placed thereon are stacked in multiple stages and supported. The movable table 240 is coupled, via a shaft sealing device 290 provided on the retort pot main body 210, to a driving shaft 285 of a crank mechanism 280 drivable by a motor 270.

When the motor 270 is driven and rotated, the driving shaft 285 of the crank mechanism 280 reciprocates the retort pot main body 210 in association with the rotation of the motor 270, and thus the movable table 240 which supports the trays 260 having the retort food 250 placed thereon is slid. The retort food is sterilized and then cooled while being slid, so that the food is suppressed from, for example, being burned during the sterilization.

SUMMARY OF THE INVENTION

For sterilizing retort food having fluid food or the like sealed therein, in Japanese Laid-Open Patent Publication No. 2008-301739, the retort food 250 is mainly slid during the sterilization to suppress the food from being burned. However, as a result of studies, the present inventors found the following. The temperature in the retort pot main body 210 is not uniform. The problem that the food may be burned during the sterilization is not limited to fluid food. Even non-fluid food is heated non-uniformly during the sterilization depending on the position thereof in the retort pot main body 210.

One reason that the food is heated non-uniformly during retort sterilization is a temperature difference described below. When hydroheat is poured on the retort food for heating in the retort pot main body 210, there is a temperature difference between a part which is exposed to hydroheat well and a part which is not. When high-temperature, high-pressure vapor (boiler vapor) is introduced into the retort pot main body 210 and the retort food is heated with the boiler vapor, there is a temperature difference between a part which is exposed to the boiler vapor well and a part which is not. Air remaining in the retort pot main body 210 acts as a heat insulator and causes heating non-uniformity, namely, non-uniform temperature distribution, in the retort pot main body 210. The temperature and the pressure of the boiler vapor introduced into the retort pot main body 210 are higher than the temperature and the pressure set in the retort pot. Therefore, the food may be heated to a higher temperature than assumed. Especially in a part exposed to the boiler vapor well, the problem of heating non-uniformity is often serious.

The air may be discharged from the retort pot main body 210 by connecting a vacuum pump (pressure decrease pump) to the inside of the retort pot main body 210. However, use of the vacuum pump needs high facility cost and also high running cost, which significantly raises the sterilization cost (or production cost) of retort food. As described above, a retort sterilization device requires high initial cost beyond comparison than that of a boil sterilization device, and use of a vacuum pump still raises the cost. In addition, even if the air in the retort pot main body 210 can be discharged, there is still heating non-uniformity between a part directly exposed to the boiler vapor well and a part which is not. In a device in which hydroheat is poured on the food, compressed air is introduced into the retort pot main body 210 to put the inside thereof into a pressurized state. Therefore, the influence of the air cannot be eliminated.

The heating non-uniformity involves a possibility that a low-temperature part of the food is not sufficiently sterilized. In addition, even if retort sterilization is performed successfully, there is a high possibility that the heating non-uniformity may spoil the taste of the food.

The present invention made in light of the above-described situation, has a main object of providing a retort sterilization device, a heating device, a heat sterilization method and a heat treatment method which have a high energy efficiency and/or are capable of suppressing heating non-uniformity.

A retort sterilization device according to the present invention includes a heating pot for accommodating retort food; and a water steam generation device for generating water steam. The heating pot is connected to the water steam generation device; the water steam generation device has a liquid path and a vapor path independent from each other, and includes a heat exchanger for performing heat exchange between liquid flowing in the liquid path and heating vapor flowing in the vapor path; the heating vapor from a boiler is introduced into the vapor path of the heat exchanger; a top end of the liquid path of the heat exchanger is connected via a water steam supply pipe to a water steam ejection section located in the heating pot; the heat exchanger is connected to a liquid container for storing the liquid to be supplied to the heat exchanger; a bottom end of the liquid path of the heat exchanger is connected to the liquid container via a communicating tube; and the liquid container is coupled to the heating pot.

In a preferable embodiment, the liquid is stored in the liquid container; and a water level of the liquid in the liquid container matches a water level of the liquid in the liquid path of the heat exchanger.

In a preferable embodiment, the liquid container is provided with a water level adjustment member for adjusting the water level of the liquid.

In a preferable embodiment, the liquid container is connected to the heating pot via a coupling pipe.

In a preferable embodiment, the liquid container includes a liquid pot main body having a top opening in an upper part thereof and a lid for sealing the top opening of the liquid pot main body; the liquid pot main body is a pressure-resistant container; a bottom part of the liquid pot main body is connected to the communicating tube; and the lid is connected to the coupling pipe.

In a preferable embodiment, the liquid container includes a liquid pot main body having a top opening in an upper part thereof; and the liquid pot main body is attached to the heating pot such that the top opening is located in the heating pot.

In a preferable embodiment, a bottom surface of the liquid pot main body is connected to the communicating tube.

In a preferable embodiment, a top lid which does not seal the top opening is provided at the top opening of the liquid pot main body.

In a preferable embodiment, the heating pot is cylindrical; and a plate on which a container for accommodating the retort food is to be placed is located in the heating pot.

In a preferable embodiment, the water steam ejection section is a sparge pipe located so as to extend in a horizontal direction in the heating pot.

In a preferable embodiment, a plurality of the water steam ejection sections are located in the heating pot.

In a preferable embodiment, the water steam ejection section is located in a lower area in the heating pot.

In a preferable embodiment, at least two of the water steam ejection sections are located in the lower area in the heating pot; and at least two of the water steam ejection sections are located in an area above the lower area in the heating pot.

In a preferable embodiment, a lower part of the heating pot is connected to a discharge pipe for discharging gas in the heating pot to outside the heating pot.

In a preferable embodiment, the discharge pipe is connected to a variable valve for varying an opened/closed state of the discharge pipe; and the discharge pipe is capable of discharging drip water from a bottom part of the heating pot.

In a preferable embodiment, the heating pot is provided with at least one of an air discharge valve for discharging air in the heating pot to outside the heating pot and a proportional valve as a pressure relief valve for adjusting an internal pressure.

In a preferable embodiment, the air discharge valve is attached to a highest part of the heating pot.

In a preferable embodiment, a heating device for heating the water steam is provided at a part of the water steam supply pipe connected to the water steam ejection section.

In a preferable embodiment, the heating device is an electric heater.

In a preferable embodiment, the retort sterilization device is a pressurization and heating device for circulating the water steam through the heat exchanger, the heating pot and the liquid container to put an internal area of the heating pot into a pressurized state.

In a preferable embodiment, the water steam generated by the water steam generation device is saturated water vapor having a minute pressure of 0.12 MPaA or less (i.e., gauge pressure of 0.0187 MpaG or less).

In a preferable embodiment, a cooling water supply pipe is connected to a part of the water steam supply pipe such that cooling water is ejected from the water steam ejection section.

In a preferable embodiment, the communicating tube for providing communication between the heat exchanger and the liquid container is branched into a first path and a second path.

In a preferable embodiment, a circulation pump for circulating the liquid is located in the second path.

A heating device according to the present invention includes a heating pot for accommodating a heating target; and a heat exchanger connected to the heating pot. The heat exchanger has a liquid path and a vapor path independent from each other, and performs heat exchange between liquid flowing in the liquid path and heating vapor flowing in the vapor path; a top end of the liquid path of the heat exchanger is connected via a first pipe to an ejection section located in the heating pot; the heat exchanger is connected to a liquid container for storing the liquid to be supplied to the heat exchanger; a bottom end of the liquid path of the heat exchanger is connected to the liquid container via a communicating tube; and the liquid container is coupled to the heating pot.

In a preferable embodiment, water steam is generated from the top end of the liquid path of the heat exchanger by the heat exchange performed by the heat exchanger; and the heating pot is provided with an air discharge valve for discharging air in the heating pot to outside the heating pot when the water steam is supplied to the heating pot.

In a preferable embodiment, a lower part of the heating pot is connected to a discharge pipe for discharging air in the heating pot to outside the heating pot.

In a preferable embodiment, the liquid is stored in the liquid container; and a water level of the liquid in the liquid container matches a water level of the liquid in the liquid path of the heat exchanger.

In a preferable embodiment, the liquid container includes a liquid pot main body having a top opening in an upper part thereof; and the liquid pot main body is attached to the heating pot such that the top opening is located in the heating pot.

In a preferable embodiment, the liquid in the liquid path of the heat exchanger is introduced from the top end of the liquid path into the heating pot via the first pipe; and the liquid in the heating pot is introduced into the liquid path via the liquid pot main body and the communicating tube.

In a preferable embodiment, the communicating tube is connected to a circulation pump for circulating the liquid.

In a preferable embodiment, the heating target is food.

A heat sterilization method according to the present invention is a method for performing heat sterilization in a pressurized state and includes the steps of locating a heating target in a heating pot; and introducing water steam into the heating pot. The water steam is generated by a heat exchanger; the heat exchanger, a liquid container for supplying liquid to the heat exchanger and the heating pot are connected to form a sealed space; and the step of introducing the water steam is carried out continuously to put an internal area of the heating pot into a pressurized state.

In a preferable embodiment, the heat exchanger, the liquid container and the heating pot are connected so as to be continuous in a loop.

In a preferable embodiment, in the step of introducing the water steam, the water steam is introduced into an area in the heating pot including a central part and an area below the central part, and air in the heating pot is discharged from an upper part thereof.

In a preferable embodiment, in the step of introducing the water steam, air in the heating pot is discharged from a lower part thereof.

In a preferable embodiment, the heating target is at least one selected from the group consisting of food packaged by a retort pouch, canned food and bottled food.

A heat treatment method according to the present invention is a method for heat-treating a heating target and includes the steps of locating the heating target in a heating pot; and introducing water steam into the heating pot. The water steam is generated by a heat exchanger; the heat exchanger, a liquid container for supplying liquid to the heat exchanger and the heating pot are connected so as to be continuous in a loop; and the step of introducing the water steam is carried out continuously to heat an internal area of the heating pot.

In a preferable embodiment, in the step of introducing the water steam, the water steam is introduced, and also air in the heating pot is discharged from an upper part thereof.

In a preferable embodiment, in the step of introducing the water steam, the water steam is introduced, and also air in the heating pot is discharged from a lower part thereof.

In a preferable embodiment, in the step of introducing the water steam, the water steam is introduced into an area in the heating pot including a central part and an area below the central part, and air in the heating pot is discharged from an upper part thereof.

In a preferable embodiment, the step of introducing the water steam into the heating pot includes introducing overheated vapor which is generated by heating the water steam generated by the heat exchanger.

In a preferable embodiment, the heating target is at least one selected from the group consisting of retort food, fish, meat, vegetable, root crop, fruit, rice, bread, tea, coffee, and tsukudani.

A heat treatment method in an embodiment uses water steam, and includes the steps of generating the water steam by a water steam generation device including a heat exchanger; introducing the water steam into a heating pot; and introducing liquid present in a bottom part in the heating pot into the heat exchanger.

In a preferable embodiment, in the step of heating in the heating pot, the water steam is circulated between the heat exchanger and the heating pot to put an internal area of the heating pot into a pressurized state.

A method for producing a fish-processed product according to the present invention includes the step of heating fish having bones in a heating pot. The heating pot is connected to a water steam generation device for generating water steam; the water steam generation device has a liquid path and a vapor path independent from each other, and includes a heat exchanger for performing heat exchange between liquid flowing in the liquid path and heating vapor flowing in the vapor path; high-pressure vapor from a boiler is introduced into the vapor path of the heat exchanger; a top end of the liquid path of the heat exchanger is connected via a water steam supply pipe to a water steam ejection section located in the heating pot; and a bottom end of the liquid path of the heat exchanger is connected to the heating pot via a communicating tube.

In a preferable embodiment, in the step of heating in the heating pot, the water steam is circulated between the heat exchanger and the heating pot to put an internal area of the heating pot into a pressurized state.

In a preferable embodiment, in the step of heating in the heating pot, the bones of the fish are softened.

In a preferable embodiment, the method further includes the steps of, after the step of heating in the heating pot; kneading the fish heated by the heating pot; and baking the kneaded fish by a high-temperature vapor baking machine.

In a preferable embodiment, in the step of kneading the fish, a seasoning is added to the heated fish; and in the step of baking by the high-temperature vapor baking machine, the kneaded fish is baked in the state of being spread to be thin.

In a preferable embodiment, the high-temperature vapor baking machine includes a second water steam generation device for generating the water steam; a heating device for heating the water steam to generate overheated vapor; and a baking chamber for baking the kneaded fish with the overheated vapor; and an ejection pipe for ejecting the overheated vapor is located in the baking chamber.

In a preferable embodiment, the high-temperature vapor baking machine further includes a belt conveyor which passes through the baking chamber; the baking chamber is an open space which is opened at an entrance and an exit for the belt conveyor; and an ejection opening of the ejection pipe is located above the belt conveyor.

Another heating device according to the present invention is a heating device using water steam and includes a heating pot for accommodating a heating target; and a water steam generation device for generating water steam. The heating pot is connected to the water steam generation device; the water steam generation device has a liquid path and a vapor path independent from each other, and includes a heat exchanger for performing heat exchange between liquid flowing in the liquid path and heating vapor flowing in the vapor path; high-pressure vapor from a boiler is introduced into the vapor path of the heat exchanger; a top end of the liquid path of the heat exchanger is connected via a water steam supply pipe to a water steam ejection section located in the heating pot; and a bottom end of the liquid path of the heat exchanger is connected to the heating pot via a communicating tube.

In a preferable embodiment, the heating device circulates the water steam between the heat exchanger and the heating pot to put an internal area of the heating pot into a pressurized state.

In a preferable embodiment, the liquid is stored in a lower part in the heating pot; and a water level of the liquid in the heating pot matches a water level of the liquid in the liquid path of the heat exchanger.

In a preferable embodiment, the heating pot includes a cylindrical main body; and includes openable/closable doors respectively at a front opening and a rear opening of the main body.

In a preferable embodiment, the water steam generated by the water steam generation device is saturated water steam having a minute pressure of 0.12 MPaA or less.

In a preferable embodiment, the heating target is fish.

A heat treatment method according to the present invention is a heating method using water steam and includes the steps of generating the water steam by a water steam generation device including a heat exchanger; introducing the water steam into a heating pot; and introducing liquid present in a bottom part in the heating pot into the heat exchanger.

In a retort sterilization device according to the present invention, the water steam generation device connected to the heating pot includes the heat exchanger, and the top end of the liquid path of the heat exchanger is connected via the water steam supply pipe to the water steam ejection section located in the heating pot. The heat exchanger is connected to the liquid container, and the bottom end of the liquid path of the heat exchanger is connected to the liquid container via the communicating tube. The liquid container is coupled to the heating pot. Therefore, a sealed space can be constructed by connecting the heat exchanger, the heating pot and the liquid container. By introducing the water steam (minute-pressure vapor) from the water steam generation device including the heat exchanger into the heating pot, the internal pressure of the heating pot can be gradually raised to put the internal area of the heating pot into a pressurized state. The water steam is basically saturated water vapor. Therefore, by introducing the water steam into the heating pot, an atmosphere of saturated water steam containing almost no air can be formed. Thus, heating non-uniformity caused by air acting as a heat insulator can be suppressed. As a result, a retort sterilization device having a high energy efficiency and/or capable of suppressing heating non-uniformity can be realized. Owing to the sealed space provided by connecting the heat exchanger, the heating pot and the liquid container, these elements have an equal internal pressure. Therefore, the water level in the heat exchanger and the water level in the liquid container can be matched to each other based on the Pascal's principle. This stabilizes the water level in the heat exchanger, and thus water steam can be generated stably and continuously.

DETAILED DESCRIPTION OF PREFERRED EMBODIMENTS

Figure 1:
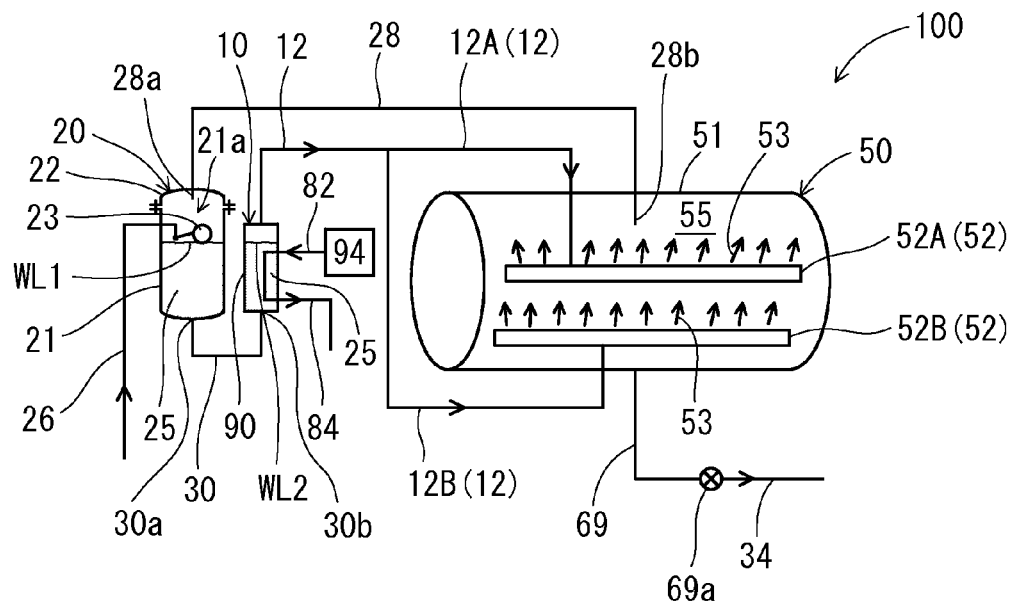
FIG. 1 is a schematic view showing a structure of a retort sterilization device (heating device) 100 in an embodiment according to the present invention.

The present inventors studied poor energy efficiency and/or heating non-uniformity of a retort sterilization device for many years. Since conventional retort sterilization devices using high-temperature pressurized vapor (boiler vapor) and hydroheat are completed per se, the present inventors considered that the defects thereof would be only alleviated by accumulating small improvements. However, the present inventors found a technique unique and quite different from the conventional common knowledge, by which heating in a pressurized state is performed using minute-pressure vapor (water steam), and thus achieved the present invention. Specifically, in order to perform retort sterilization by heating in a pressurized state using water steam (minute-pressure saturated vapor), the present inventors succeeded in generating a pressurized state easily in a heating pot without using compressed air. A retort sterilization device using boiler vapor has problems in terms of taste and appearance; for example, a retort odor (e.g., odor generated by denaturing of protein) may be generated, or discolorization (to a dull brown color) may occur, when a heating target is heated by high-temperature boiler vapor which flows into the device. Even in a retort sterilization device in which hydroheat is poured on food, a retort odor (e.g., odor generated by denaturing of protein)

may be generated, or discolorization (to a dull brown color) may occur, after the heating due to heating non-uniformity or the like.

Hereinafter, with reference to the drawings, embodiments of the present invention will be described. In the following drawings, elements having substantially identical functions will be represented with identical reference numerals for simplifying the description. The present invention is not limited to the following embodiments.

FIG. 1 is a schematic view showing a structure of a retort sterilization device (heating device) 100 in an embodiment according to the present invention. The retort sterilization device 100 in this embodiment is a heating device capable of performing sterilization with pressurization and heating (retort sterilization) on retort food sealed in a bag formed of a heat-resistant resin film or the like. The heating device 100 in this embodiment is a device (vapor heating device) for heating a heating target by use of water steam (minute-pressure saturated vapor). Especially when the heating target is food (retort food in this example), the heating device 100 in this embodiment is a vapor-system food heating device.

The retort sterilization device 100 in this embodiment includes a heating pot 50 and a water steam generation device 10 for generating water steam. The heating pot 50 is connected to the water steam generation device 10. A heat exchanger 90 is connected to a liquid container 20 for storing liquid 25 to be supplied to the heat exchanger 90. The liquid container 20 is coupled to the heating pot 50.

Figure 2:
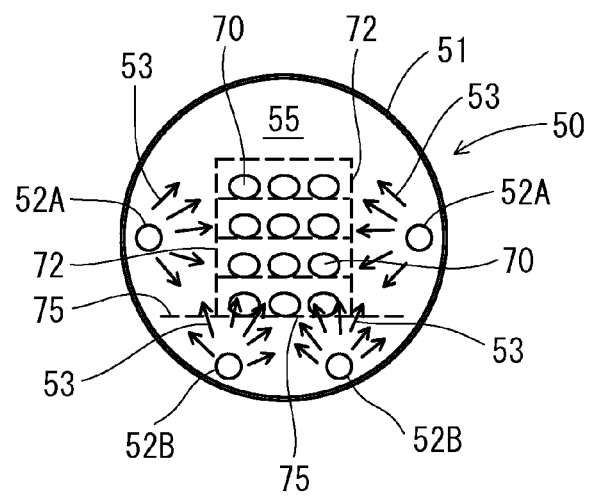
FIG. 2 is a cross-sectional view schematically showing a structure of a heating pot 50 in an embodiment according to the present invention.

FIG. 2 is a cross-sectional view schematically showing a structure of the heating pot 50 in this embodiment. The heating pot 50 in this embodiment is a retort pot (heating pot) in which retort food 70 is to be placed. In the example shown in FIG. 2, a plate 75 on which containers (trays) 72 for accommodating the retort food 70 are to be placed is located in the heating pot 50. In this example, the retort food 70 is accommodated in each of the trays 72, and the containers 72 are stacked in multiple stages and are located in an internal area 55 of the heating pot 50. In the example shown here, the retort food 70 is accommodated in the containers 72, but the food 70 may be in any other form as long as being located in the internal area 55 of the heating pot 50.

The retort food in this embodiment is food which is to be treated with heating in a pressurized state, and is, for example, food packaged in a retort pouch. A retort pouch is generally formed of a film obtained by a lamination process and having a polypropylene layer on the side of the food and a polyester (PET) or any other synthetic resin layer or an aluminum foil on the outer side. The retort pouch can contain the food inside in a sealed state by blocking air, moisture and light. Retort pouches (retort packaging containers) are available in a flat bag (flat, envelope-like bag; used for, for example, curry, "gyudon" (steamed rice topped with stewed beef), etc.), a standing pouch (bag having an extended bottom; used for, for example, stew, etc.), and a molded container (lunch box-type plastic container having a sealing film applied on top thereof; used, for example, retort rice, etc.).

The "retort food" in this embodiment means food to be sterilized with pressurization and heating, and encompasses food packaged in a retort pouch, canned food, and bottled food. Food provided as retort food may be any type of food which is suitable to be produced into retort food; for example, fish, meat, vegetables, root crops, fruits or the like. The "retort food" in this embodiment is not limited to food for humans, and may be food for pets or animal retort food. "Retort sterilization" (heating in a pressurized state) for producing retort food is not limited to being used for the purpose of heat sterilization treatment, and may be used for the purpose of softening the food. Representative examples of the retort food include curry (retort curry), stew, soup, porridge, pasta sauce, ingredients of "donburi" (ingredients of toppings of boiled rice), rice (retort rice), hamburger steak, meat ball, and the like.

Retort treatment (retort sterilization) is, on principle, sterilization performed in the state where a central part of the food in the container is pressurized and heated at 120° C. for 4 minutes or by use of an equivalent amount of heat (the temperature and time are adjusted in accordance with the type of food). This treatment can annihilate spore bacteria and also is considered to eliminate the botulinum bacteria, which are most heat-resistant among general food-poisoning bacteria. In the food industry, the numerical value which represents the effectiveness of sterilization is F value (F value=1 at 120° C. for 1 minute). Usually, sterilization of an F value of 5 about to 10 is performed.

The heating pot 50 in this embodiment is a pressure-resistant heating container and is cylindrical. The heating pot 50 in this embodiment is formed of, for example, a stainless steel material. Since the heating pot 50 is cylindrical, a structure strong against the pressure is provided. However, the heating pot 50 is not limited to being cylindrical, and may be of any other shape as long as acting as a retort pot. The heating pot 50 is preferably cylindrical because a heating pot of any other shape (e.g., shape having a quadrangular cross-section) is heavier than a cylindrical heating pot. Herein, the term "cylindrical" is not limited to a precisely cylindrical shape in a geometric sense. A shape having a slightly deformed circular cross-section (e.g., elliptical, egg-shaped), namely, a substantially cylindrical shape, is usable.

Figure 3:
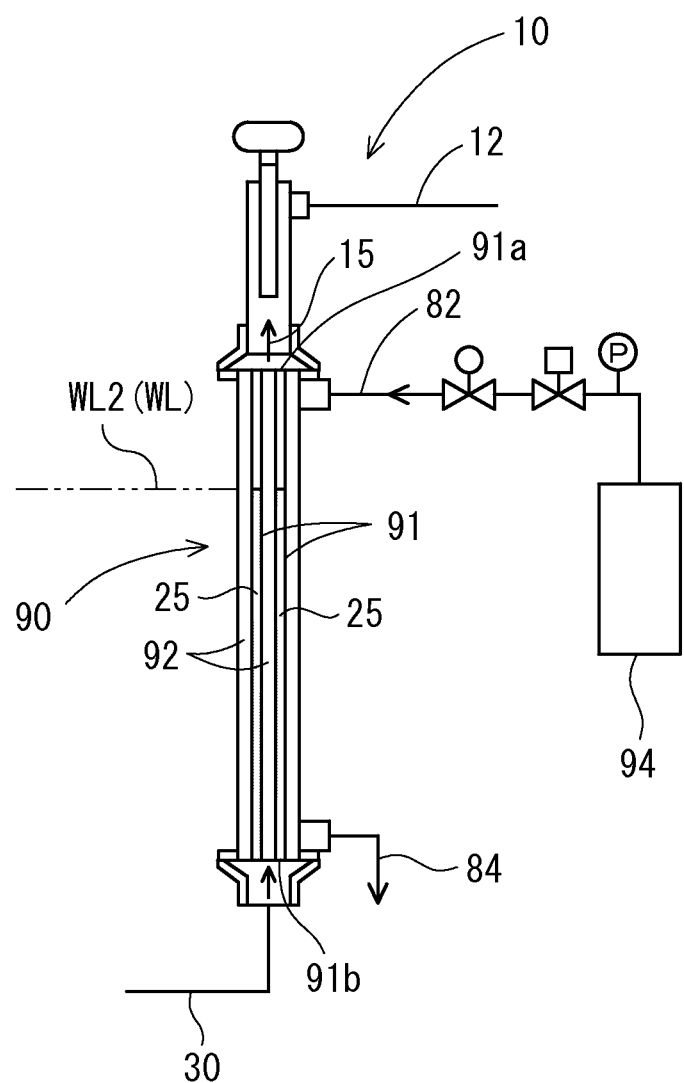
FIG. 3 shows a structure of a water steam generation device 10 (heat exchanger 90) in an embodiment according to the present invention.
Figure 4:
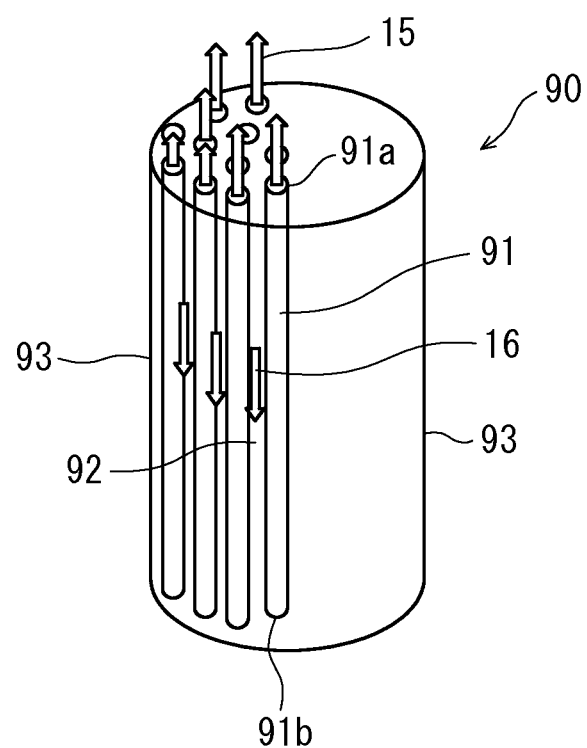
FIG. 4 is a schematic view showing a structure of the heat exchanger 90 in an embodiment according to the present invention.

The water steam generation device 10 in this embodiment includes the heat exchanger 90. The structure of the heat exchanger 90 in this embodiment is shown in FIG. 3 and FIG. 4. FIG. 3 shows a cross-sectional structure of the heat exchanger 90 together with a boiler 94. FIG. 4 is a perspective view schematically showing an internal structure of the heat exchanger 90.

The heat exchanger 90 in this embodiment includes a liquid path 91 and a vapor path 92 independent from each other. Heat is exchanged between liquid (in this example, water) flowing in the liquid path 91 and heating vapor (in this example, steam vapor) flowing in the vapor path 92.

As shown in FIG. 3, the heating vapor from the boiler 94 (boiler vapor or high-pressure vapor) is introduced into the vapor path 92 of the heat exchanger 90. Specifically, the high-pressure vapor from the boiler 94 is introduced into the vapor path 92 of the heat exchanger 90 via a boiler pipe 82. In the heat exchanger 90, the heat of the heating vapor flowing in the vapor path 92 is transferred to the liquid present in the liquid path 91 and thus heat is exchanged. In the heat exchanger 90, the heat is exchanged when the heating vapor (thermal medium) and the liquid (medium to be heat-exchanged) cross each other in a non-contact manner. Thus, water is boiled and water steam (minute-pressure saturated vapor) 15 is generated. The heating vapor after the heat exchange in the heat exchanger 90 is discharged via an exhaust steam pipe 84.

As shown in FIG. 4, the heat exchanger 90 in this embodiment includes a plurality of liquid paths 91 located in an outer casing 93. In this embodiment, the outer casing 93 is generally cylindrical, and the liquid paths 91 are formed of heat transmission pipes. The heat transmission pipes forming the liquid paths 91 are formed of a material for transferring the heat of the thermal medium (steam) to the heat exchange target (in this example, water), and are formed of, for example, metal pipes (e.g., stainless steel). The liquid paths (heat transmission pipes) 91 extend in a longitudinal direction (axial direction) of the cylindrical outer casing 93. In this embodiment, the liquid paths 91 extend in the axial direction and are located parallel to each other with an interval in a circumferential direction of the cylindrical outer casing 93. A space between the liquid paths (heat transmission pipes) 91 acts as the vapor path 92 through which the thermal medium (steam) 16 passes. The water steam 15 is generated and transferred from tip ends 91a of the liquid paths 91 of the heat exchanger 90.

As shown in FIG. 1, the water steam generation device 10 including the heat exchanger 90 is connected via a water steam supply pipe 12 to a water steam ejection section 52 located in the internal area 55 of the heating pot 50. Therefore, the water steam 15 generated from top ends 91a of the liquid paths 91 of the heat exchanger 90 is transferred through the water steam supply pipe 12, is introduced into the internal area 55 of the heating pot 50, is ejected from the water steam ejection section 52, and is released into the internal area 55 of the heating pot 50 (arrow 53).

In this embodiment, at least one water steam ejection section 52 is located in the internal area 55 of heating pot 50. In the structure of this embodiment, a plurality of water steam ejection sections 52 (52A, 52B) are located in the internal area 55 of the heating pot 50. The water steam ejection sections 52 in this embodiment are each a sparge pipe having a plurality of ejection openings. In the example shown here, the water steam ejection sections 52 are located so as to extend in a horizontal direction in the internal area 55 of the heating pot 50. In this example, the water steam ejection sections 52 (sparge pipes) are located in a longitudinal direction of the cylindrical heating pot 50.

In the structure shown in FIG. 2, at least one of the water steam ejection sections 52 (52B) in this embodiment is located in a lower area of the internal area 55 of the heating pot 50. In the example shown here, two sparge pipes 52B are located in the lower area of the internal area 55 of the heating pot 50. In this embodiment, the "lower area" of the internal area 55 of the heating pot 50 refers to an area close to a bottom surface of the internal area 55 of the heating pot 50. In the example shown in FIG. 2, the "lower area" is an area below the plate 75. Also in the example shown in FIG. 2, the water steam ejection sections 52 (52A) are located above the lower area in the heating pot 50. In this example, the water steam ejection sections 52 (52A) are located in a central area of the heating pot 50 (a horizontal plane passing the center of the cylindrical heating pot 50 or in the vicinity thereof). In the example shown here, two lower sparge pipes 52B and two central sparge pipes 52A are located in the internal area 55 of the heating pot 50. The two sparge pipes 52A are located in left-right symmetry to each other, and the lower sparge pipes 52B are also located in left-right symmetry to each other. It is possible to locate one or a plurality of (e.g., two) water steam ejection sections (sparge pipes) 52 in an upper area in the heating pot 50 (area close to a top surface of the internal area 55 of the heating pot 50). Namely, according to the structure of this embodiment, it is possible to locate a plurality of water steam ejection sections (sparge pipes) 52 in the entire internal area 55, namely, in the upper, lower, left and right parts therein.

Bottom ends 91b of the liquid paths 91 of the heat exchanger 90 are connected to the liquid container 20 via a communicating tube 30. More specifically, one end 30a of the communicating tube 30 is connected to the liquid container 20, and the other end 30b of the communicating tube 30 is connected to the heat exchanger (especially, the bottom ends 91b of the liquid paths 91). Therefore, the liquid (water) 25 in the liquid container 20 can be transferred to the communicating tube 30. Then, the water steam is generated from the liquid paths 91 of the heat exchanger 90 and the water level in the liquid paths 91 of the heat exchanger 90 is lowered. In accordance with this, and so as to compensate for this, the liquid in the communicating tube 30 is transferred toward the bottom ends 91b of the liquid paths 91 of the heat exchanger 90.

In the structure shown in FIG. 1, the liquid container 20 includes a liquid pot main body 21 having an opening 21a in an upper part thereof and a lid 22 for sealing the opening 21a of the liquid pot main body 21. The liquid pot main body 21 is a pressure-resistant container and can withstand a predetermined pressure during the operation. A bottom part of the liquid pot main body 21 is connected to the communicating tube 30. The lid 22 for closing the opening 21a in the upper part of the liquid pot main body 21 is connected to a coupling pipe 28. One end 28a of the coupling pipe 28 is located in the liquid container 20, and the other end 28b of the coupling pipe 28 is located in the internal area 55 of the heating pot 50.

In the structure shown in FIG. 1, a lower part of the heating pot 50 is connected to a discharge pipe 69. The discharge pipe 69 in this embodiment can discharge drip water (obtained as a result of the vapor being deteriorated, liquid generated from the heating target) stored in the bottom part in the heating pot 50. The discharge pipe 69 is opened or closed by a variable valve 69a. The discharge pipe 69 (and the variable valve 69a) in this embodiment can be used to discharge gas (air and/or vapor) in the heating pot 50 to the outside. The discharge pipe 69 and the variable valve 69a can adjust the internal pressure of the heating pot 50.

In the structure shown in FIG. 1, the liquid container 20 is sealed by the liquid pot main body 21 and the lid 22. Alternatively, the communicating tube 30 and the coupling pipe 28 may be connected to each other in the liquid container 20 of an integrated form without providing the lid 22. Still alternatively, the lid 22 may be attached to a part, other than the top surface (for example, a side surface), of the liquid pot main body 21 included in the liquid container 20.

In the retort sterilization device 100 in this embodiment, the liquid container 20 is connected to the heating pot 50 via the coupling pipe 28. The liquid path 91 of the heat exchanger 90 is connected to the heating pot 50 via the water steam supply pipe 12. The liquid path 91 of the heat exchanger 90 is connected to the liquid container 20 via the communicating tube 30. Therefore, a sealed space can be constructed by connecting the heat exchanger 90, the heating pot 50 and the liquid container 20. By introducing the water steam (minute-pressure vapor) 15 generated by the water steam generation device 10 including the heat exchanger 90 into the heating pot 50, the pressure of the internal area 55 of the heating pot 50 can be gradually raised with the introduced water steam 53 to realize a pressurized state.

In the sealed structure having the sealed space, the pressure is equal at any position because of the Pascal's principle. Therefore, as long as the heat exchanger 90, the heating pot 50, the liquid container 20 and the pipes connecting these have a pressure-resistant structure, the internal pressure of the sealed structure is gradually raised while being equal.

This will be described in more detail. Even if the vapor (water steam) generated from the heat exchanger 90 is of a minute pressure, a sealed space such as a balloon, a tire or the like can be put into a pressurized state by continuously supplying gas to the sealed space. When the pressure of the pressurized state is entirely in synchronization, the pressure is gradually raised, and as a result, a pressure higher than that of the introduced vapor (water steam) can be achieved. Namely, since the Pascal's principle works in a sealed structure, when the internal pressure of the heating pot 50 is slightly raised by the introduction of minute-pressure water steam, the same level of pressure is generated also in the heat exchanger 90. As a result, as the minute-pressure water steam is gradually introduced, the internal pressure of the heat exchanger 90 is raised along with the internal pressure of the heating pot 50 (and of the liquid container 20). As a result, even if the pressure of the water steam generated from the heat exchanger 90 is about 0.12 MPaA or less (i.e., gauge pressure of 0.0187 MpaG or less), the internal pressure of the heating pot 50 can be made higher than 0.12 MPaA. Specifically, the internal pressure of the heating pot 50 can be made in the range of an absolute pressure of 0.12 MPaA or a pressure close thereto to about 0.2 MPaA (or 0.3 MPaA). The temperature can be raised to about 120° C., which is up to about 90% (about 80 to 90%) of the temperature of the thermal source for heat exchange. Typically, water steam (minute-pressure vapor) having a pressure of 0.13 MPaA or less (in one example, 0.105 to 0.12 MPaA) is used to put the internal area 55 of the heating pot 50 into a pressurized state in which retort sterilization can be performed (e.g., about 0.2 MPaA).

In addition, water steam is basically saturated water vapor. Therefore, by introducing the water steam into the heating pot, an atmosphere of saturated water vapor containing almost no air can be formed. Thus, heating non-uniformity caused by air acting as a heat insulator can be suppressed. As a result, a retort sterilization device which has a high energy efficiency and/or can suppress heating non-uniformity can be realized. Boiler vapor contains impurities, but water steam does not contain impurities. On this point also, the water steam is advantageous.

In the sealed space formed of the heat exchanger 90, the heating pot 50 and the liquid container 20, the pressure is substantially equal at any position. Therefore, the water level (WL1) in the liquid container 20 can be matched to the water level (WL2) in the liquid path 91 of the heat exchanger 90 via the communicating tube 30 based on the Pascal's principle. Specifically, in a pre-pressurization state, the water level (WL1) in the liquid container 20 can be matched to the water level (WL2) in the liquid path 91 of the heat exchanger 90 owing to the atmospheric pressure based on the Pascal's principle. In a pressurized state, the water level (WL1) in the liquid container 20 can be matched to the water level (WL2) in the liquid path 91 of the heat exchanger 90 owing to the internal pressure of the sealed space, again based on the Pascal's principle.

Since the water level (WL2) in the liquid path 91 of the heat exchanger 90 can be controlled simply and stably, vapor (water steam) can be introduced stably. Introduction of high-temperature, high-pressure boiler vapor is difficult to be controlled precisely. By contrast, according to the retort sterilization device 100 in this embodiment, vapor introduction can be controlled precisely in accordance with the control procedure. One reason for this is that the minute-pressure water vapor (water steam) has a low flow rate and thus is easily controllable. As a result, according to the retort sterilization device 100 in this embodiment, a sterilization and/or heating process can be allowed to proceed precisely, stably and simply.

In the structure shown in FIG. 1, the liquid container 20 is provided with a water level adjustment member 23 for adjusting the water level (WL1) of the liquid 25. The water level adjustment member 23 is formed of, for example, a water level indicator (e.g., floating sphere). The liquid container 20 is connected to a pipe (e.g., water pipe) 26 for supplying liquid (water). According to the structure of this embodiment, water can be supplied via the pipe (e.g., pipe having a pressure higher than the internal pressure; typically, water pipe) 26 based on the water level WL1 indicated by the water adjustment member (water level indicator) 23. The water adjustment member 23 is not limited to a simple water level indicator (e.g., floating sphere), and may be an electronically controllable device which can adjust the water level WL1 to a prescribed or constant level.

As described above, according to the retort sterilization device 100 in this embodiment, boiler vapor (pressurized vapor for heating) from the boiler 94 is not introduced as it is into the internal area 55 of the heating pot 50, but the water steam 15 from the water steam generation device 10 is introduced into the internal area 55 of the heating pot 50. The water steam generation device 10 generates the water steam (saturated water vapor) 15 having a minute pressure (e.g., 0.12 MPaA or less). Owing to having such a minute pressure, the water steam 15 is transferred slowly in the water steam supply pipe 12 and introduced into the internal area 55 of the heating pot 50. Herein, the "water steam" refers to minute-pressure vapor, not high-pressure vapor such as boiler vapor. In other words, the "water steam" in this embodiment is not high-temperature, high-pressure steam vapor, but is minute-pressure vapor (e.g., vapor having a pressure of 0.12 MPaA or less). Herein, the "water steam" is characterized in being minute-pressure vapor, and may be any vapor which rises from boiled water (water vapor). The "water steam" is not limited to being in a state of small water drops which appear like a white smoke. Namely, the "water steam" may be in a state like a white smoke or may be transparent.

According to the technological common knowledge, in order to realize a high-temperature, high-pressure heating environment in a heating pot, high-pressure gas (vapor, air) is introduced into the heating pot to realize a high-temperature, high-pressure state. The higher the pressure is, the easier it is to realize a high-temperature heating environment. Against such an assumption, the present inventors continuously introduces the water steam 15, which is minute-pressure vapor, into the heating pot 50, so that the internal area 55 of the heating pot 50 is put into a pressurized state. Namely, the present inventors constructs a pressurized state in the heating pot 50 in an approach different from the technological common knowledge in the art.

According to the heating device 100 in this embodiment, the water steam 15 having a pressure of 0.11 MPaA or 0.12 MPaA is continuously introduced, and thus the internal area 55 of the heating pot 50 can be provided with a pressure of, for example, 0.15 MPaA to 0.25 MPaA (in one example, 0.15 MPaA (111° C.)), 0.20 MPaA (120° C.) or 0.30 MPaA (133° C.). Since the liquid is automatically supplied to the liquid path 91 of the heat exchanger 90 via the communicating tube 30, the water steam 15 can be continuously introduced into the heating pot 50 by the heat exchange performed by the heat exchanger 90. In one example, boiler vapor having a pressure of 0.30 MPaA (133° C.) is used to generate water steam (clean steam) 15 having a pressure of 0.12 MPaA (104° C.) by use of the heat exchanger 90 (in other words, the water steam generation device 10 of a vapor indirect heating system) and to raise the pressure and the temperature of the water steam 15 by the above-described mechanism (synchronous pressure raising method), so that the internal area 55 of the heating pot 50 is put into a pressurized state with the water steam 15. Specifically, the pressure of the internal area 55 of the heating pot 50 can be raised to, for example, 0.20 MPaA (120° C.) by the pressure and temperature rise performed with the water steam 15 provided by the heat exchanger 90.

In the heating pot 50 of the heating device 100 in this embodiment, heating by vapor (heating by the water steam 15) was performed at a heating temperature of 110 to 120° C. and a pressure of 0.14 MPaA to 0.20 MPaA for, for example, 20 to 40 minutes. As a result, retort sterilization of an F value of 6 was performed on retort food. The heating temperature and the heating time (or pressure) are not limited to these, and may be selected appropriately. For example, retort sterilization may be performed in a shorter time than 20 minutes or a longer time than 40 minutes depending on the conditions. Specifically, the heating time varies in accordance with the specific heat, size or the like of the heating target. Therefore, an appropriate heating time may be selected in accordance with the target.

Food provided as a product by a retort production method is often not as tasty as usual cooked food, which is produced by a method other than the retort production method. A conceivable reason for this is that the main object of the retort production method is to sterilize at a high temperature in a pressurized state (retort sterilization) (namely, sterilization is the main object) but is not to improve the state of the heated food. A treatment performed by a conventional retort sterilization device heats the food at a high temperature in a pressurized state, which often results in generation of a retort odor (e.g., odor generated by denaturing of protein) after the heating. In addition, when boiler vapor (about 130 to 150° C.) is directly introduced into the heating pot, there is a high possibility that non-uniformity is caused in raising the temperature in the heating pot. In the case where pressurized air (compressed air) is used for raising the pressure, heating non-uniformity is caused also by an influence of introduction of pressurized air acting as a heat insulator.

By contrast, according to the retort sterilization device (heat treatment method) in this embodiment, water steam can be continuously introduced into the heating pot 50 by use of the heat exchanger 90. By gradually raising the pressure and the temperature through the introduction of the water steam 15, the temperature in the heating pot 50 in this embodiment and the temperature of the retort food 70 in the heating pot 50 can be raised in a matched state. (Note that the core temperature of the retort food 70 is raised in a delayed manner.) As a result, an effect provided by the stable temperature rise of the food 70, an effect provided by the uniform heating environment in the heating pot 50 (reduction of the heating non-uniformity), an effect provided by the clean vapor (water steam) with no use of boiler vapor, an effect provided by the heating environment in a low air state (high thermal conductivity owing to a small amount of air), an effect provided by the heating environment having high concentration water vapor similar to the state inside a basket steamer, and the like are obtained. The specific heat of saturated water vapor is higher than the specific heat of dry air. Therefore, the heating environment having high concentration water vapor containing substantially no air is preferable for heating food (especially, retort sterilization).

In a structure in which the water steam ejection section 52 is located in the lower area (or the central area) of the internal area 55 of the heating pot 50, the following advantages are provided. When the water steam ejection section 52 is located in the lower area (or the central area) of the internal area 55 of the heating pot 50 in a structure in which an air discharge valve for discharging air in the internal area 55 of the heating pot 50 to the outside is located in the upper area in the heating pot 50, the water steam 53 is transferred to the lower area of the internal area 55 of the heating pot 50 during an initial period of the introduction of the water steam 53, because the water steam 53 formed of water vapor has a higher specific gravity than that of the air. As the reaction to the introduction of the water steam 53, the air initially present in the internal area 55 of the heating pot 50 is discharged via the air discharge valve provided in, for example, the upper area in the heating pot 50. Next, as the water steam 53 is introduced, the water steam 53 fills the heating pot 50 from a relatively lower area to a relatively upper area thereof in terms of the concentration of the water steam 53. As the water steam 53 is introduced, the air in the heating pot 50 is discharged via the air discharge valve.

In the case where boiler vapor (about 130 to 150° C.) is directly introduced into the heating pot 50, the air in the heating pot 50 cannot be discharged for the following reasons. The high-temperature, high-pressure boiler vapor introduced into the heating pot 50 is transferred at quite a high rate in the heating pot 50, and therefore it is dangerous to open the heating pot 50 with an electromagnetic valve. Even if the heating pot 50 is opened, it is difficult to discharge only the air, and both of the air and the boiler vapor are discharged outside. There is another problem that since the internal pressure rapidly becomes high due to the volume expansion of air, it is difficult to put the boiler vapor into the heating pot 50. Even if an air discharge valve is provided in the heating pot 50, the air cannot be discharged with priority at the time of introduction of the boiler vapor because the boiler vapor is transferred while being diffused at a high rate in the heating pot 50 and thus is mixed with the air. Therefore, with the method of directly introducing boiler vapor into the heating pot, the air needs to be discharged by a vacuum pump before the boiler vapor is introduced, in order to realize appropriate heating control. Use of a vacuum pump requires facility cost and energy cost. In addition, it loses a lot of energy to repeat the steps of putting the internal area 55 of the heating pot 50 into a vacuum state by the vacuum pump, raising the internal pressure of the heating pot 50 with the boiler vapor, returning the internal pressure to normal pressure for removing the boiler vapor, and then putting the internal area 55 of the heating pot 50 into a vacuum state again for another cycle of heating. The structure of the retort sterilization device 100 in this embodiment can solve such a poor energy efficiency. It is convenient that the air discharge valve attached to the heating pot 50 in this embodiment has a structure in which air can be naturally discharged by a pressure difference between the inside and the outside of the heating pot 50.

In the case where the water steam ejection section 52 is located in the central area in the heating pot 50, as well as in the case where the water steam ejection section 52 is located in the lower area in the heating pot 50, the water steam 53 is transferred to the lower area in the heating pot 50 because of the specific gravity difference between the water steam 53 and air. Therefore, an effect that the air is discharged at the time of introduction of the water steam 53 is provided. In the case where the water steam ejection section 52 is located in the central area in the heating pot 50, it is easy to spray the water steam 53 to the food (retort food) 70 which is put in the central part (central position) in the heating pot 50. This provides an effect in terms of the heating efficiency and the sterilization efficiency. As shown in FIG. 2, in the case where the water steam ejection sections 52 are located in both of the lower area and the central area in the heating pot 50, both of the effect of discharging the air at the time of introduction of the water steam 53 and the effect of uniformizing the heating temperature in the heating pot 50 can be provided.

The water steam ejection section 52 may be provided in the upper area in the heating pot 50. In the case where the water steam ejection section 52 is provided in the central area and/or the upper area in the heating pot 50, the water steam 53 is transferred to the lower area in the heating pot 50 because of the specific gravity thereof. Therefore, the discharge pipe 69 provided on the lower part of the heating pot 50 can be opened so as to discharge the air along with the flow of the transferring water steam 53.

In the retort sterilization device 100 shown in FIG. 1, the liquid container 20 is located outside the heating pot 50. The retort sterilization device 100 is not limited to this, and may have another structure. Specifically, as shown in FIG. 5, the liquid container 20 may be attached to the heating pot 50.

Figure 5:
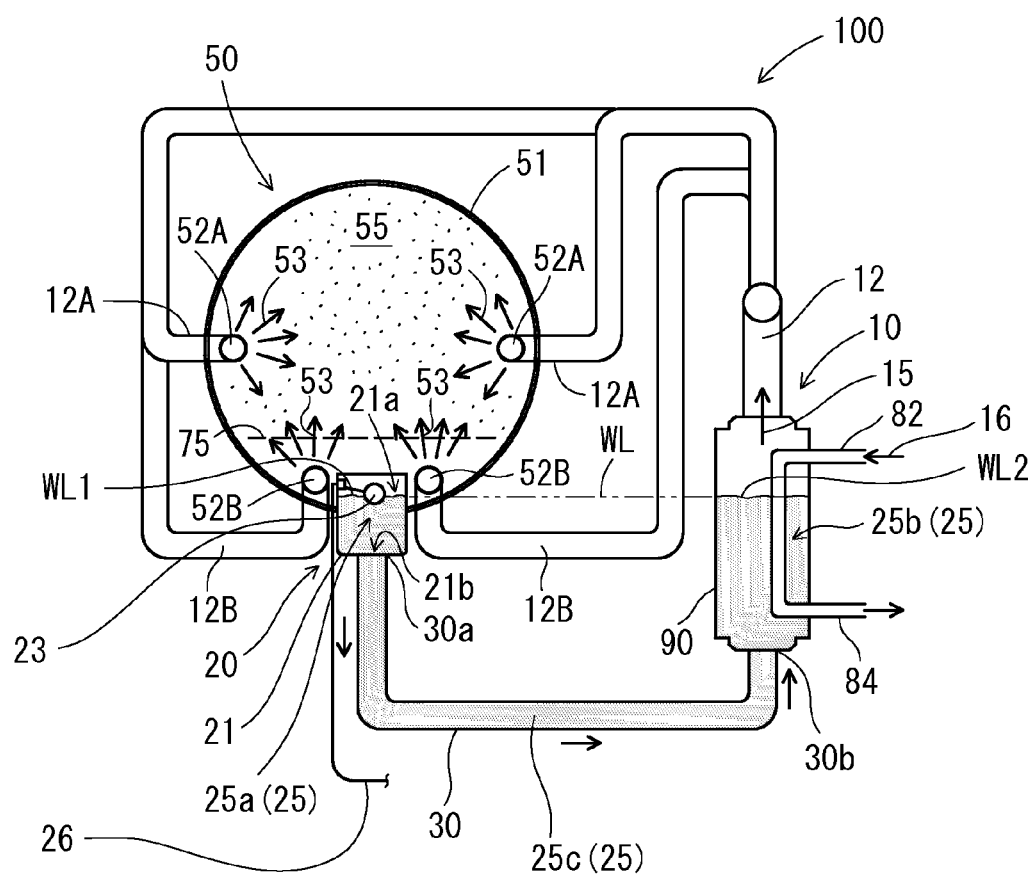
FIG. 5 is a schematic view showing a structure of a retort sterilization device (heating device) 100 in an embodiment according to the present invention.

In the retort sterilization device 100 shown in FIG. 5, the liquid container 20 includes a liquid pot main body 21 having a top opening 21a. The liquid pot main body 21 is attached to the heating pot 50 such that the top opening 21a of the liquid pot main body 21 is located in the internal area 55 of the heating pot 50. Namely, the liquid container 20 is attached to the lower part (bottom surface) of the heating pot 50, and the top opening 21a of the liquid pot main body 21 is exposed to the internal area 55 of the heating pot 50.

In the structure shown in FIG. 5, a bottom surface 21b of the liquid pot main body 21 is connected to the communicating tube 30, and the communicating tube 30 is connected to the heat exchanger 90 (especially, the bottom end 91b of the liquid path 91 of the heat exchanger 90). In such a structure in which the liquid container 20 is attached to the heating pot 50 also, the heat exchanger 90, the heating pot 50, and the liquid container 20 are connected to each other to form a sealed space. By introducing the water steam 15 (minute-pressure vapor) 15 from the water steam generation device 10 including the heat exchanger 90 into the heating pot 50, the pressure of the internal area 55 of the heating pot 50 can be gradually raised with the introduced water steam 53 to realize a pressurized state.

According to the retort sterilization device 100 shown in FIG. 5 also, the water level (WL1) in the liquid container 20 (liquid pot main body 21) and the water level (WL2) in the heat exchanger 90 (liquid path 91 of the heat exchanger 90) can be matched to each other by the internal pressure of the sealed space being equal, namely, based on the Pascal's principle. Specifically, as the amount of liquid (water) 25b in the liquid path 91 of the heat exchanger 90 is decreased along with the generation of the water steam 15, liquid (water) 25a in the liquid container 20 is automatically supplied to the liquid path 91 of the heat exchanger 90 via the communicating tube 30 (liquid 25c). Therefore, the water levels of the liquid 25 (WL1 and WL2) can be adjusted to be equal to each other.

According to the structure shown in FIG. 5, the liquid container 20 (liquid pot main body 21) may be connected to the liquid supply pipe (water pipe) 26 for supplying tap water or the like. Water can also be supplied via a pipe (e.g., pipe having a pressure higher than the internal pressure; typically, water pipe 26) based on the water level WL1 indicated by the water level adjustment member (water level indicator) 23. The water adjustment member 23 is not limited to a simple water level indicator (e.g., floating sphere), and may be an electronically controllable device which can adjust the water level WL1 to a prescribed or constant level.

According to the retort sterilization device 100 in this example, the liquid generated in the heating pot 50 (encompassing condensed water steam) reaches the liquid pot main body 21. The liquid 25 (25a) in the liquid pot main body 21 can be used as the liquid 25 (25b) to be provided to the heat exchanger 90. Namely, according to the retort sterilization device 100 shown in FIG. 5, the water steam 15 is circulated between the heat exchanger 90 and the heating pot 50 (more accurately, the water steam 15 and the liquid in the communicating tube 30 are circulated), so that the internal area 55 of the heating pot 50 can be put into a pressurized state. By this circulation heating system, the water steam 15 is made reusable. Therefore, a high efficiency retort sterilization device with less waste of the liquid (water) can be realized. In the retort sterilization device 100 in this embodiment, the vapor may be discharged outside via the discharge pipe 69 equipped with the variable valve 69a, so that the heating pot 50 is driven while the pressure therein is adjusted, in addition to the liquid being positively reused.

The liquid 25 (25a) generated in the heating pot 50 and reaching the liquid pot main body 21 is warm water. Therefore, as compared with the case where cooling water is heated by the heat exchanger 90, the energy efficiency can be improved. Namely, according to the retort sterilization device 100 in this example, thermal energy which would be otherwise disposed of can be reused. In addition, according to the structure in this example, drop waste liquid generated in the internal area 55 of the heating pot 50 can also be treated simply. Thus, multi-faceted advantages are provided.

Now, with reference to FIG. 6 through FIG. 10, the structure of the retort sterilization device 100 in this embodiment will be described in more detail. The retort sterilization device 100 shown in FIG. 6 through FIG. 10 is of a preferable example embodying the retort sterilization device 100 in this embodiment, and the retort sterilization device 100 in this embodiment is not limited to such a structural example.

Figure 6:
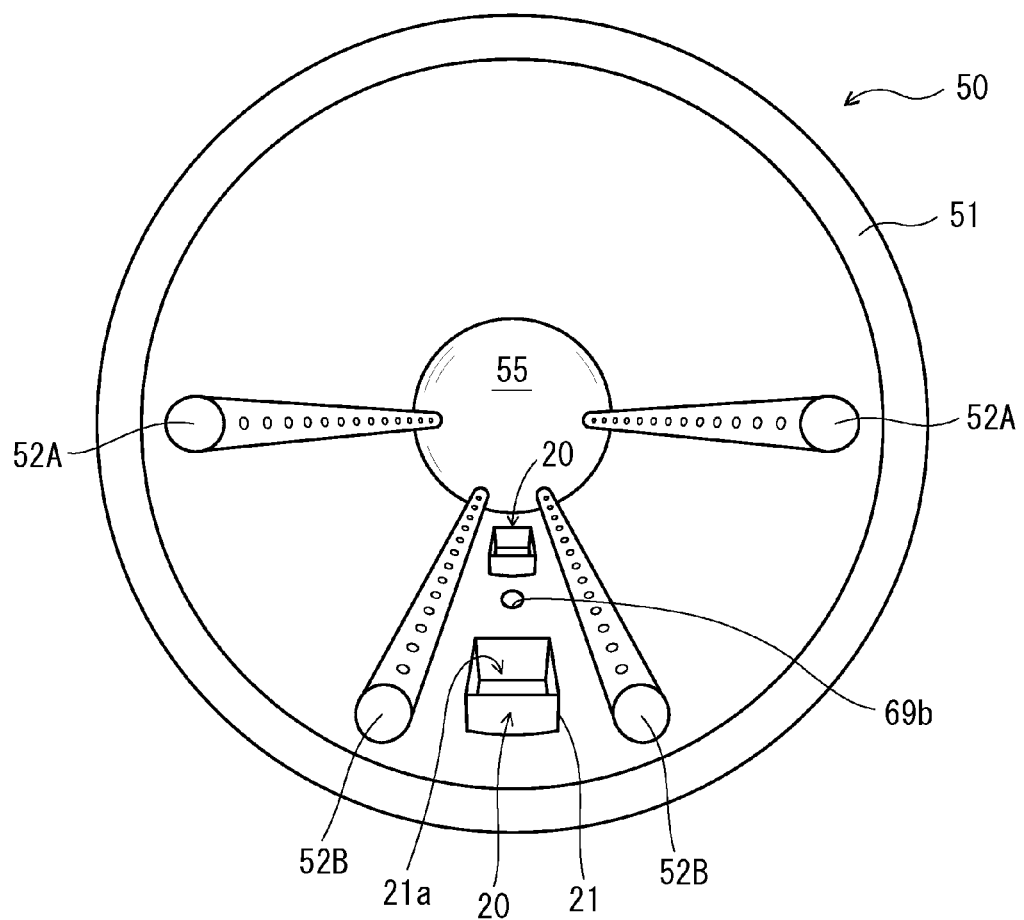
FIG. 6 is a schematic view showing an internal structure of the heating pot 50 in an embodiment according to the present invention.

FIG. 6 shows an internal structure of the heating pot 50. A pot main body 51 of the heating pot 50 has a cylindrical (or generally cylindrical) shape having a circular cross-section, and is formed of, for example, stainless steel. In the internal area 55 of the heating pot 50, the plurality of water steam ejection sections 52 (52A, 52B) are located. The water steam ejection sections 52 are formed of pipes (sparge pipes) having vapor (water steam) ejection openings located at an equal interval. The water steam ejection sections 52 are located in the longitudinal direction of the cylindrical heating pot 50, so that the water steam 53 is ejected into the internal area 55 of the heating pot 50 as uniformly as possible.

The pipes forming the water steam ejection sections 52 may extend so as to include a curved part, or extend in a meandering manner, instead of extending straight in the longitudinal direction (or horizontal direction). Alternatively, the pipes forming the water steam ejection sections 52 may extend in a spiral manner in the internal area 55 of the heating pot 50, or a plurality of such pipes extending in a circumferential direction in the internal area 55 of the heating pot 50 may be coupled to each other. Even in a structure in which the pipes forming the water steam ejection sections 52 extend straight, the water steam 53 can be sprayed uniformly, but the spraying uniformity of the water steam 53 can be possibly improved when the pipes extend to include a curved part, extend spirally, or extend to include a circular part.

In the structural example shown in FIG. 6, the pipes forming the water steam ejection sections 52 are located so as to contact the inner wall of the heating pot 50. The structure of the pipes is not limited to this. For example, the pipes may extend so as to pass through the internal area 55 of the heating pot 50. The water steam ejection sections 52 are not limited to having a form of pipe, and may be in any other form. The water steam ejection sections 52 may be, for example, through-holes formed in the pot main body 51 of the heating pot 50, through which the water steam 53 can be ejected. Alternatively, the water steam ejection sections 52 may be formed of sprinkler-like members or disc-like members having a through-hole, from which the water steam 53 can be ejected.

A pipe for supplying water (tap water or cooling water) may be connected to the water steam ejection sections 52, so that water (cooling water) is sprayed from the water steam ejection sections 52. Such a water spraying mechanism can act as a cooling mechanism of the heating pot 50. The water spraying mechanism may have the following structure, for example. A switch valve and a water pipe are attached to a part of the water steam supply pipe 12 connected to the water steam ejection sections 52, so that tap water (or any other type of water) can be introduced by switching the switch valve. In this manner, the cooling mechanism can be provided by a simple structure. Instead of allowing water to flow in the water steam ejection sections 52, an independent cooling water pipe (sparge pipe) may be located, so that water (cooling water) can be sprayed into the heating pot 50. Alternatively, a sprinkler device may be located. In the example shown in FIG. 6, an opening (connection end) 69b of the discharge pipe 69 is shown. Sprayed cooling water or the like can be discharged through the opening 69b of the discharge pipe 69.

In addition, the liquid pot main body 21 included in the liquid container 20 shown in FIG. 6 has a rectangular (or parallelepiped) shape, but the shape of the liquid pot main body 21 is not limited to this. For example, the liquid pot main body 21 may have a cylindrical shape having the opening 21a in the upper part thereof or a polygonal shape. In the structural example shown in FIG. 6, a top end of the liquid pot main body 21 projects from the inner wall of the heating pot 50, but the liquid pot main body 21 is not limited to this. The top end of the liquid pot main body 21 may be flush with the inner wall of the heating pot 50.

A top lid which covers, but does not seal, the top opening 21a of the liquid pot main body 21 may be located. This top lid can prevent rubbish or foreign objects from entering the internal area 55 of the heating pot 50. Instead of the top lid, a porous member formed of an air-permeable mesh-like or net-like member may be located so as to cover the top opening 21a of the liquid pot main body 21.

Figure 7A:
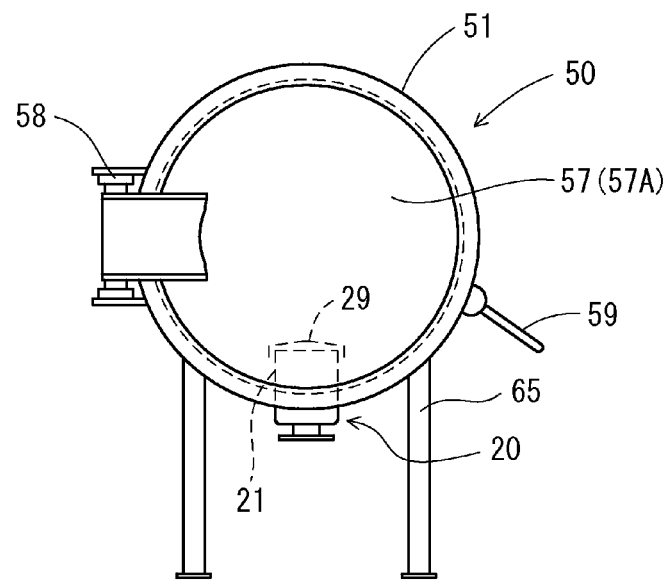
FIG. 7A and FIG. 7B are respectively a front view and a side view showing a structure of the retort sterilization device 100 in an embodiment according to the present invention.
Figure 7B:
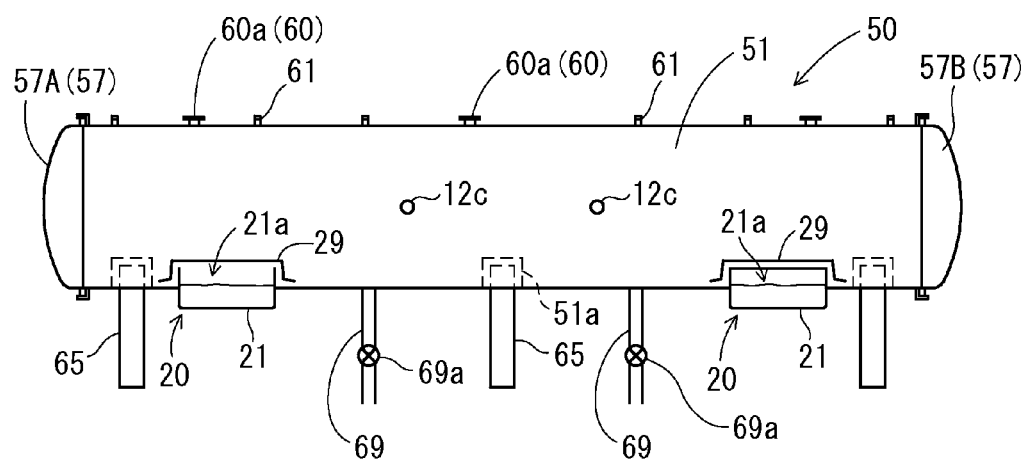

FIG. 7A and FIG. 7B are respectively a front view and a side view (cross-sectional view) showing a structure of the heating pot 50 in this embodiment. As shown in FIG. 7A, a door 57 (57A) for closing a front opening of the pot main body 51 of the heating pot 50 is provided on the front side thereof. The door 57 is openable/closable by hinges 58, and can be locked by a lever 59. In this structural example, as shown in FIG. 7B, a door 57 (57B) for closing a rear opening of the pot main body 51 of the heating pot 50 is provided on the rear side thereof. The heating pot 50 having openable/closable doors 57A and 57B on the front and rear sides thereof allows a heating target to be put into, or taken out of, the heating pot 50 through both of the front and rear doors. This can improve the work efficiency of the production line. Needless to say, the heating pot 50 may have one openable/closable door (e.g., door 57A) through which food (retort food) may be put into, or taken out of, the heating pot 50.

As shown in FIG. 7B, air discharge valves 60a (60) are provided on an upper part (especially, on a highest part) of the heating pot 50. In this example, a plurality of discharge valves 60 are provided on the heating pot 50, so that air can be discharged from the heating pot 50 as uniformly as possible. In this embodiment, there is no specific limitation on the structure or the type of the air discharge valves 60, and any valve which can appropriately discharge air (and/or internal vapor) while keeping the internal area 55 of the heating pot 50 in a pressurized state (air vent) is usable. For example, as the discharge valve 60 for discharging air from the device (pot), an automatic valve (automatic air vent) is preferable. For example, an air vent for discharging air from a vapor pipe or a device (e.g., an air discharge valve using the technology of thermostatic steam trap) is usable. A device for manually discharging air (and/or internal vapor) may be provided. In this embodiment, in order to control the pressure of the internal area 55 of the heating pot 50 positively and more precisely, an electromagnetic relief valve may be provided, so that the internal pressure of the heating pot 50 can be adjusted. In the example shown in FIG. 7B, the air discharge valves 60a are provided on the highest part of the heating pot 50. It is not absolutely necessary that the air discharge valves 60a are provided on the highest part, and there is no specific problem as long as the air discharge valves 60a are provided on the upper part. Relief valves 60 and 69 may be provided on both of the upper part and the lower part of the heating pot 50. On the upper part, the air discharge valve 60 for discharging air (and/or internal vapor) may be provided; and on the lower part, a drain or the discharge pipe 69 for discharging the internal vapor may be provided. Through the discharge pipe 69, gas (air and/or water vapor) in the heating pot 50 can be discharged by adjusting the valve (variable valve 69a).

In FIG. 7B, safety valves 61 are also provided on the upper part (especially, the uppermost part) of the heating pot 50. In the case where a sealed container having a high internal pressure is heated, a safety valve prevents from the internal pressure from becoming excessively high and thus prevents the container from being broken. Since the retort sterilization device 100 in this embodiment uses the water steam 53, which is minute-pressure vapor, the risk that the internal pressure is raised to break the heating pot 50 is quite low, but the safety valves 61 are provided for safety. The internal pressure of the heating pot 50 can also be decreased by opening or closing the discharge pipe 69 using the variable valve 69a.

In this example, top lids 29 for covering the top openings 21a of the liquid pot main bodies 21 included in the liquid containers 20 are shown. Each of the top lids 29 is located so as to cover, but not to seal, the liquid pot main body 21. The pot main body 51 of the heating pot 50 is supported by support rods (support table) 65, and securing members 51a for securing the support rods 65 are formed in an outer circumferential surface of the pot main body 51 of the heating pot 50. In the pot main body 51 of the heating pot 50, through-holes 12c through which the water steam supply pipes (vapor supply pipes) 12 extend from outside to the inside of the pot main body 51 are formed. In the heating pot 50, various sensors (temperature sensor, pressure sensor, etc.) are located. The sensors are connected to a control device (control board) for controlling the driving of the retort sterilization device 100. According to the structure of this embodiment, the control device is used to adjust the internal pressure by use of an electric proportional valves located on the upper part or on each of the upper part and the lower part of the heating pot 50, and also to control the boiler vapor to be taken into the heat exchanger 90. In this manner, both of the internal temperature and the internal pressure of the heating pot 50 can be adjusted. A proportional valve (proportional control valve or electromagnetic proportional control valve) can control a fluid in a proportional manner in addition to being controlled to be opened or closed. By changing a control signal to be sent to the proportional valve (proportional control valve), the flow rate of the flowing fluid can be continuously controlled in the range of 0 to 100% with respect to the maximum flow rate.

FIG. 7A and FIG. 7B do not show the heat exchanger 90, but at least one heat exchanger 90 is provided for one heating pot 50. In this embodiment, a plurality of (e.g., three) heat exchangers 90 are provided for one heating pot 50, so that a large amount of water steam 53 can be supplied to the heating pot 50 as uniformly as possible, although the number of the heat exchangers 90 depends on the size and volume of the heating pot 50. The size of the heating pot 50 is, for example, as follows, although there is no specific limitation thereon. The diameter of the heating pot 50 is, for example, 50 cm to 2 m or greater, and the length of the heating pot 50 in the longitudinal direction is, for example, 50 cm to 10 m or greater.

Figure 8:
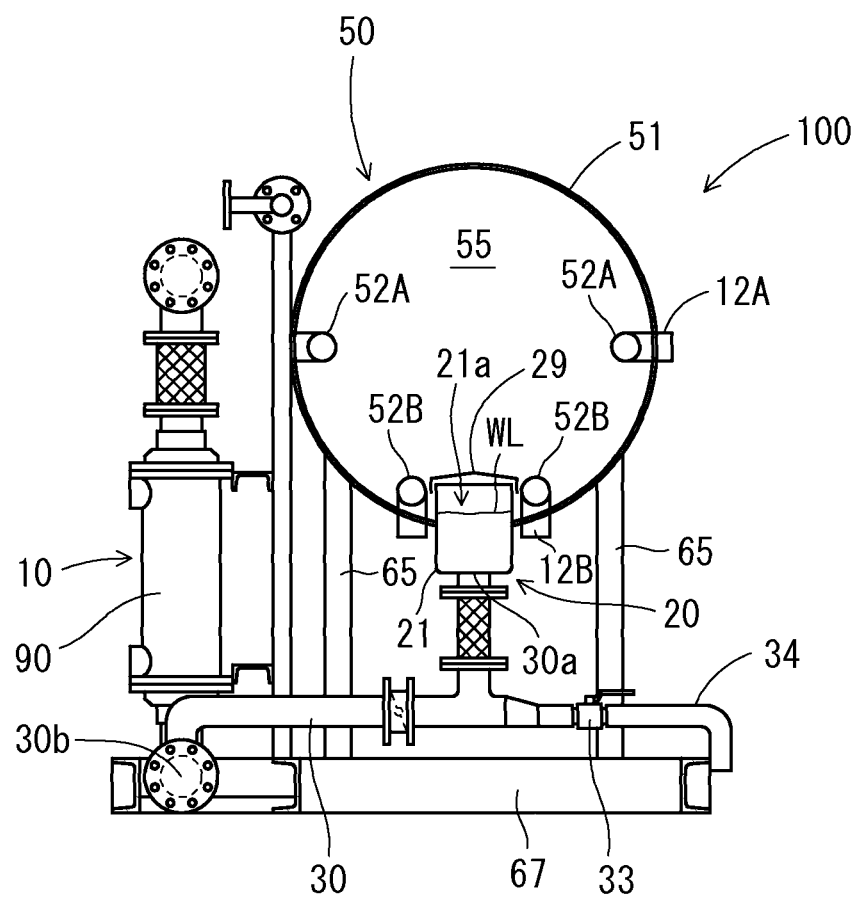
FIG. 8 shows a structure of a retort sterilization device 100 in an embodiment according to the present invention.

FIG. 8 shows a structural example in which the liquid container 20 attached to the heating pot 50 and the heat exchanger 90 are connected to each other via the communicating tube 30. The communicating tube 30 extending from the heat exchanger 90 is connected to the liquid container 20, and the opening 21*a* of the liquid container 20 is exposed to the internal area 55 of the heating pot 50. The communicating tube 30 is coupled to a drain pipe 34 for discharging the liquid from the internal area 55 of the heating pot 50, so that the waste liquid can be discharged from the drain pipe 34 via an openable/closable valve 33. In the case where the discharge pipe 69 is connected to the heating pot 50, the drain pipe 34 may be connected to the discharge pipe 69. The support rods 65 for supporting the heating pot 50 are coupled to a base 67.

Figure 9:
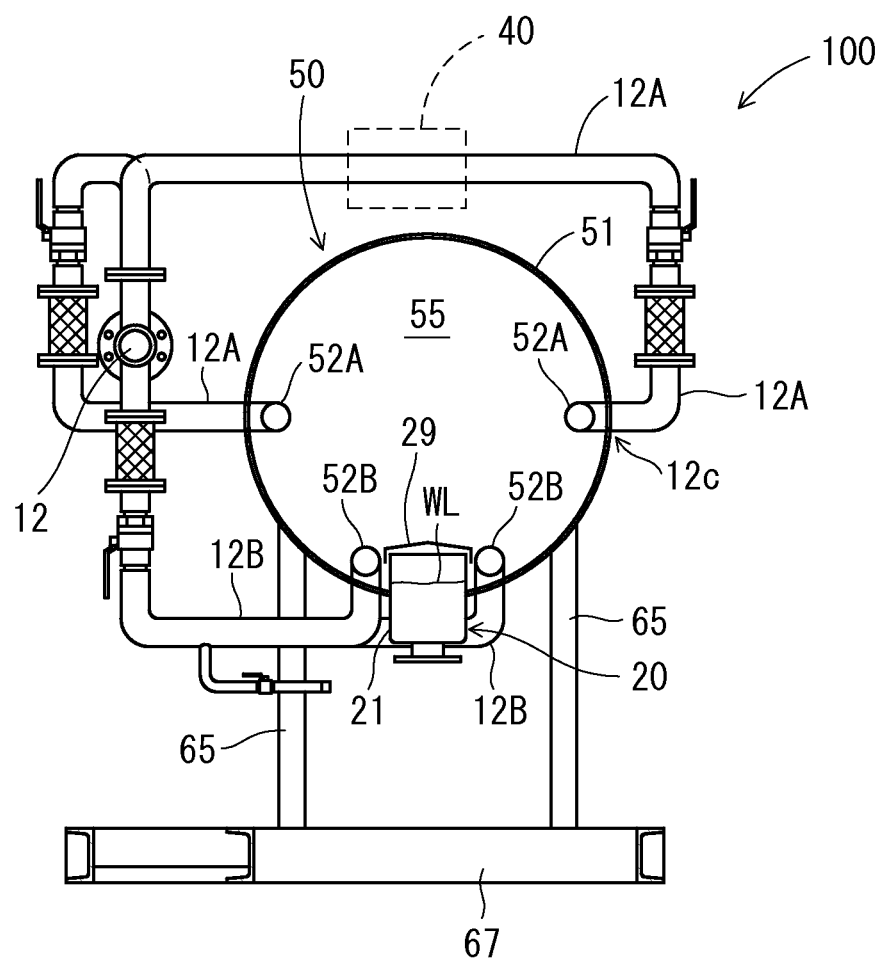
FIG. 9 shows a structure of a retort sterilization device 100 in an embodiment according to the present invention.

FIG. 9 shows a structural example of the heating pot 50, the water steam supply pipes 12 (12A, 12B), and the water steam ejection sections 52 (52A, 52B). In the example shown in FIG. 9, the one, common water steam supply pipe 12 is branched into a first water steam supply pipe 12A and a second water steam supply pipe 12B, which are introduced into the internal area 55 of the heating pot 50. In the example shown in FIG. 9, the first water steam supply pipe 12A and the second water steam supply pipe 12B are each branched into a plurality of (two) pipes. One of the first water steam supply pipes 12A extends so as to stride over the heating pot 50. The first water steam supply pipes 12A are not limited to having this structure, and one of the first water steam supply pipes 12A may extend below the heating pot 50.

A heating device 40 for heating the water steam may be provided in a part of the water steam supply pipes 12. In the case where the heating device 40 is located in a part of the water steam supply pipes 12, the temperature of the water stream flowing in the water steam supply pipes 12 can be raised. Specifically, the heating device 40 can act as an additional means (heating means) for adjusting the temperature in the retort sterilization device 100 to a predetermined level. The heating device 40 is, for example, an electric heater. The electric heater 40 in this embodiment is, for example, an electric heater of about several kilowatts (e.g., plug heater, flange heater, etc.)

By heating the water steam by use of the heating device 40, overheated water steam can be generated from the water steam. When usual high-temperature, high-pressure boiler vapor is heated by an electric heater, the heating efficiency is not high because the flow rate of the boiler vapor is high. According to the structure of this embodiment, water vapor (minute-pressure vapor) having a low flow rate is heated by the heating device (e.g., electric heater). Therefore, the overheated vapor can be generated at a high efficiency. In an atmosphere of the overheated vapor of the heating pot 50, food can be retort-heated (retort-sterilized) or heated. In the heating device 40, heating is performed at substantially the same internal pressure as the atmospheric pressure (e.g., internal pressure of 1.2 atmospheric pressure or less) during the operation. Therefore, a safe operation in terms of the pressure can be guaranteed.

Figure 10:
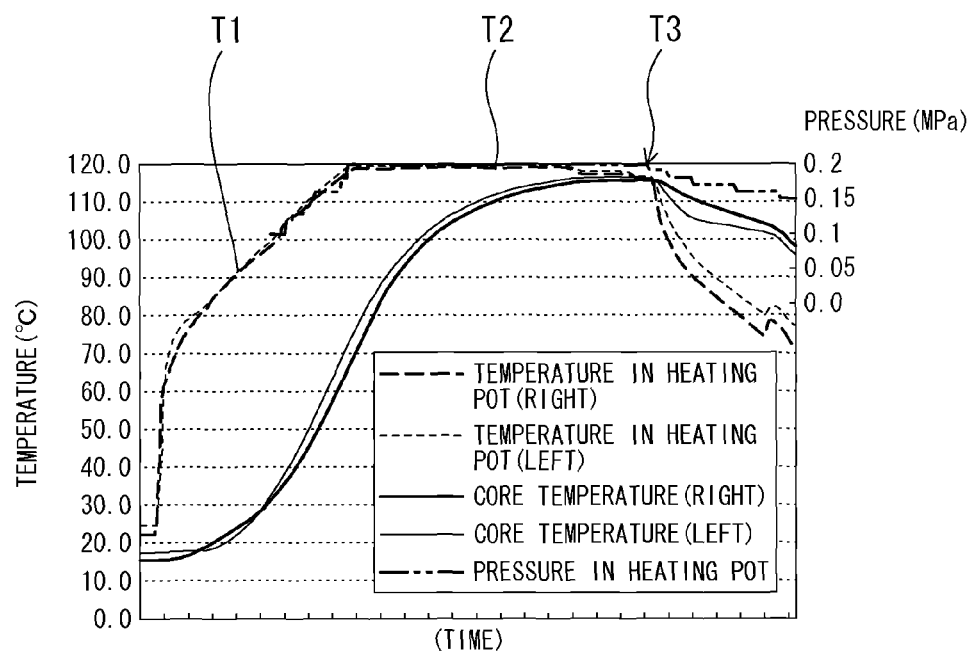
FIG. 10 is a graph showing the temperature and the pressure in the case where the retort sterilization device 100 is operated.

Now, with reference to FIG. 10, operation results of the retort sterilization device 100 in this embodiment will be described. FIG. 10 is a graph showing the results of the operation of the retort sterilization device 100. The graph of FIG. 10 shows the temperature of the internal area 55 of the heating pot 50 (in a right part and a left part in the heating pot 50) and the core temperature of the food 70 located therein (in a right part and a left part in the heating pot 50), and also shows the pressure of the internal area 55 in the heating pot 50. In this example, the results of the operation of heating bottled food are shown. One graduation of the horizontal axis is about 4 minutes. In this example, water steam having an absolute pressure of 0.12 MPaA or less (e.g., about 0.11 MPaA) is continuously introduced, and the pressure is raised by accumulating the pressure of the water steam continuously added (zone T1). After the pressure reaches a predetermined level (0.20 MPaA), the internal pressure is controlled to be constant at the level (zone T2).

When the retort sterilization device 100 starts operating, the internal pressure is raised. Along with this, the temperature in the heating pot 50 is raised. It is seen that at the time of start and while the temperature is rising (zone T1), the temperature difference between parts (right part, left part) in the heating pot 50, which would be usually large, is suppressed small. Namely, it is seen that the temperature in the heating pot 50 is controlled with high uniformity. It is also seen that while the temperature in the furnace is adjusted to the set temperature (about 120° C.) (zone T2), the temperature difference between the parts (right part, left part) in the heating pot 50 is very small. Along with the temperature rise in the heating pot 50, the core temperature of the food (right part, left part) also rises. Since the dispersion in the temperature between the parts in the heating pot 50 (right part, left part) is very small, the dispersion in the core temperature of the food is also very small. Since the core temperature rises smoothly along with the temperature rise in the furnace, very appropriate heating treatment can be performed. Owing to this, food can be processed (heat-treated) to be tasty.

When the heating of the retort sterilization is finished, the internal temperature is controlled to be decreased (point T3). Along with this, the temperature in the furnace and the core temperature of the food are decreased. During the process of decreasing the internal temperature, pressurized air is introduced into the heating pot 50 by a compressor and the air is kept pressurized in the furnace until the core temperature of the product is decreased to a certain temperature (e.g., 70° C.), in order to prevent the bag from being broken. In a final step, the internal pressure of the heating pot 50 is made the atmospheric pressure and the heated product is taken out. Thus, the retort sterilization treatment is finished.

As can be seen from FIG. 10, according to the retort sterilization device 100 in this embodiment, the pressure and the temperature in the heating pot can be controlled precisely. A conceivable reason why such precise control can be performed is that since a minute pressure (e.g., 0.12 MPaA or less) is repeatedly added by the water steam to the pressure in the heating pot 50, the pressure, temperature, specific volume, and amount of heat (latent heat) of the internal area 55 of the heating pot 50 do not change much. There is also the following advantage. Since the water steam has a low flow rate, the introduction of the water steam does not disturb the air in the internal area 55 of the heating pot 50, and the air can be smoothly released by the air discharge valve 60 (or the discharge pipe 69) provided on the heating pot 50.

By contrast, when the system of directly putting boiler vapor into the heating pot is used, at the time of making settings on the control device, the temperature and the pressure can each be regulated to a predetermined value. However, it is actually very difficult to remove the dispersion in the pressure and the temperature between parts in the heating pot. This will be described in more detail. With the system of directly putting boiler vapor, when boiler vapor having a pressure of 0.3 MPaA flows in (usually, boiler having a pressure of about 0.4 MPaA is used), namely, when the boiler is put into the heating pot from the pipe, the pressure of the vapor temporarily changes, for example, from 0.3 MPaA to 0.1 MPaA. The temperature of the vapor changes from 133° C. to 100° C. The specific volume changes from 0.605 m$^3$/kg to 1.673 m$^3$/kg. The amount of heat (latent heat) changes from 516.8 kcal/kg to 539.6 kcal/kg. It is very difficult to control the heating temperature using a thermal medium (boiler vapor) having characteristics which change significantly when being put into the heating pot from the pipe. In order to continuously put boiler vapor as an external thermal source, the thermal source needs to have a pressure higher than the set pressure. This is also a factor of restriction. With the system of directly putting boiler vapor, boiler vapor having a pressure of 0.3 MPaA (133° C.) flows in. Therefore, the difference between the temperature in the heating pot and the core temperature of the product is 100° C. or higher when the temperature starts rising. The temperatures of an area contacting the boiler vapor and an area not contacting the boiler vapor keep rising while having a large temperature difference. When the core temperature of the product becomes about 110° C., the temperature starts rising proportionally. However, the temperature difference is still about 13° C. (the temperature of the boiler vapor is 133° C., whereas the set temperature for the product is 120° C.), and therefore there is a problem that the production quality is not constant.

The system of directly putting boiler vapor into the heating pot has the following problem. The conditions for the boiler vapor are changed significantly. Therefore, in the state where vapor having a pressure higher than the set pressure and a temperature higher than the set temperature flows in, a rapid pressure decrease or a rapid temperature decrease may occur in the heating pot (in the furnace). Against such a state, it is needed to maintain the set temperature. In such a state, precise temperature control is almost impossible even if the flow rate of the boiler vapor is controlled by an electromagnetic valve. As a result, the temperature non-uniformity occurs. Since the vapor having a temperature higher than the set temperature is present, the food is partially burned or overdone. This promotes denaturing of protein, which leads to poor taste or odor.

Similarly, with the system of putting hydroheat into the heating pot by use of compressed air, at the time of making settings on the control device, the temperature and the pressure can each be regulated to a predetermined value. However, it is actually very difficult to remove the dispersion in the pressure and the temperature between parts in the heating pot. Both of the systems use a pressurized boiler vapor or compressed air, and therefore have more serious problems in terms of driving safety and control on the temperature and the pressure than the system of this embodiment which uses minute-pressure vapor (water steam).

With the system of directly putting boiler vapor into the heating pot, a strong alkaline boiler compound (e.g., of about pH 11 to 13) is used when the boiler vapor is generated. Therefore, the strong alkaline component may be mixed into the boiler vapor and attached to the bag of the product or the like. By contrast, according to the structure of this embodiment, water steam obtained by boiling water by heat exchange is introduced into the heating pot 50. Therefore, the problem of corrosion by such a strong alkaline component can be avoided.

With the system of putting hydroheat into the heating pot by use of compressed air, the compressed air needs to be introduced and the pressure of the air needs to be returned to the atmospheric pressure each time. This involves a problem of poor energy efficiency. In addition, hydroheat drops below the heating pot because of the gravity, and thus it is necessary to keep supplying new hydroheat to the heating pot and keep spraying the hydroheat to the food (retort food). This also decreases the energy efficiency. According to the technique of the embodiment of the present invention, water steam drifts in the heating pot 50, and therefore is highly advantageous as compared with the system which requires constant spraying of hydroheat to the food. According to the technique of the embodiment of the present invention, the temperature and the pressure can be raised by continuously supplying water steam acting as a heating source. Therefore, it is not necessary to use compressed air, and also introduction of air acting as a heat insulator can be avoided. This is also a great contribution technologically.

Therefore, according to the structure of this embodiment, the retort sterilization device (heating device) 100 having a high energy efficiency and/or capable of suppressing heating non-uniformly can be realized.

In the above embodiment, the retort sterilization device 100 capable of performing retort sterilization by use of water steam has been described. By modifying the retort sterilization device 100 in this embodiment, a hydroheat circulation-system retort sterilization device (heating device) can be realized.

Figure 11:
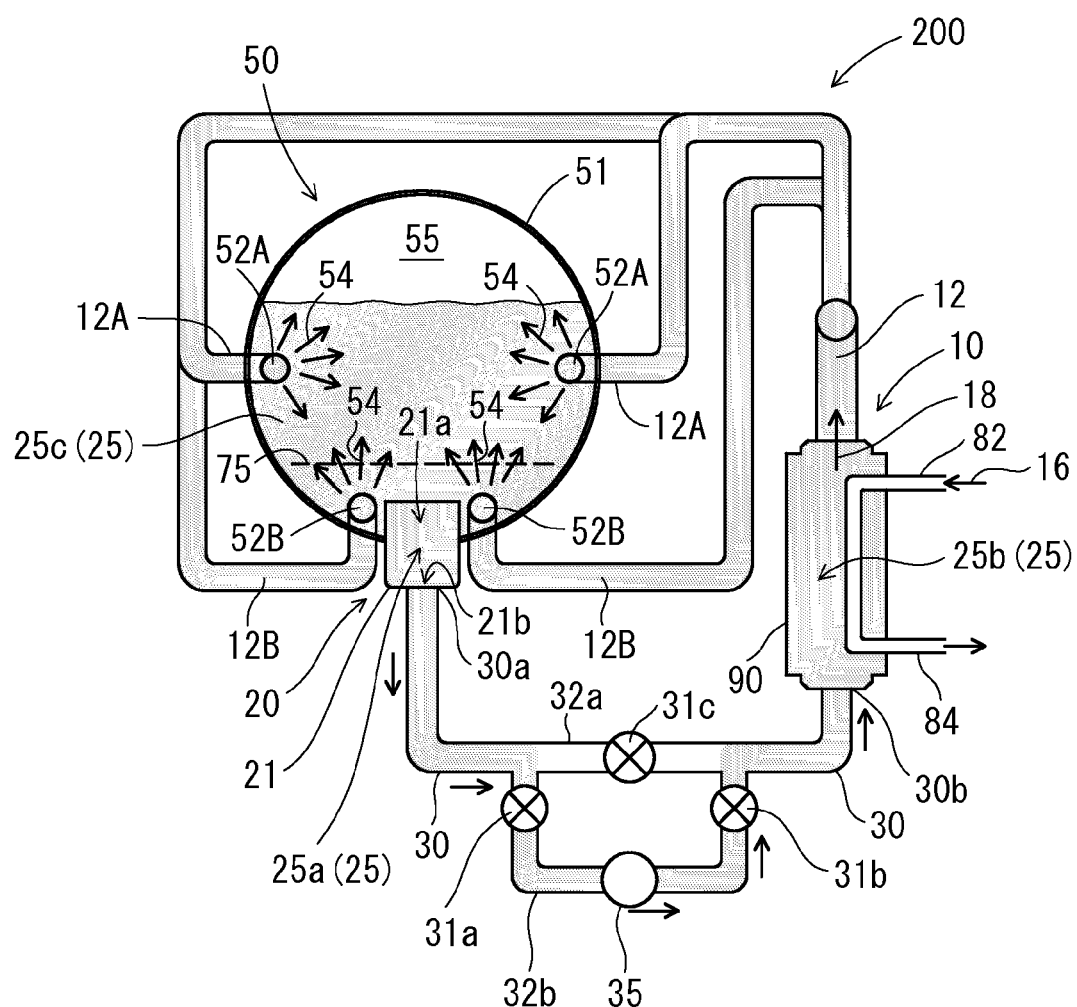
FIG. 11 is a schematic view showing a structure of a retort sterilization device (heating device) 200 in an embodiment according to the present invention.

FIG. 11 schematically shows a structure of a retort sterilization device 200 in an embodiment according to the present invention. The retort sterilization device 200 shown in FIG. 11 has substantially the same basic structure as that of the retort sterilization device 100 shown in FIG. 5. According to the retort sterilization device 200 in this embodiment, heating water (hydroheat or warm water) can be circulated through the heat exchanger (hydroheat generation device) 90, the heating pot 50, and the communicating tube 30.

The communicating tube 30 of the retort sterilization device 200 includes a second path 32b separately from a first path 32a. In the second path 32b, a circulation pump 35 for circulating liquid (hydroheat) 25 is provided. Namely, the communicating tube 30 includes the second path 32b branched from the first path 32a used as the communicating tube 30 for uniformizing the water level. According to this structure, when the circulation pump 35 is operated in the state where an openable/closable valve 31c of the first path 32a is closed while openable/closable valves 31a and 31b of the second path 32b are opened, the liquid (hydroheat) 25 can be circulated.

Specifically, when the water steam ejection sections (in this example, hydroheat ejection sections) 52 (in this example, 52A) are filled with the liquid 25 (25c) up to an upper part thereof, the liquid 25 (25b) is heated by heat exchange performed by the heat exchanger 90 and thus becomes high-temperature hydroheat 18. The hydroheat 18 flows in the water steam supply pipes (in this example, hydroheat supply pipes) 12 and is supplied as hydroheat 54 to the internal area 55 of the heating pot 50 from the water steam ejection sections (in this example, hydroheat ejection sections) 52. Next, the liquid 25c in the internal area 55 of the heating pot 50 flows in the liquid container 20 (liquid pot main body 21) and enters the communicating tube 30. Then, the liquid 25a is circulated by the circulation pump 35.

According to the retort sterilization device 200 in this embodiment, heating is performed with hydroheat. Therefore, the heat transmission efficiency is still improved as compared with heating with water steam. In the case where the pressure in the heating pot 50 is high, hydroheat heating treatment at a temperature exceeding 100° C. can be performed. As shown in FIG. 11, in the case where, for example, half or more of the internal area 55 of the heating pot 50 is filled with hydroheat 25 (25c), the food (retort food) can be entirely heated and thus the heating non-uniformity does not occur. The temperature of the hydroheat can be adjusted in the range from a low temperature (room temperature to less than 100° C.) to a high temperature exceeding 100° C. In the case where the structure shown in FIG. 11 is applied to food which is not retort-packaged, a boiling step (stewing, boiling) with hydroheat can be performed.

After the food is heat-treated by the retort sterilization device 200, the hydroheat 25 may be transferred to another tank to empty the heating pot 50, and then the food (retort food) may be taken out. For performing heat treatment by the retort sterilization device 200 again, the hydroheat 25 may be introduced into the communicating tube 30 again from the another tank, so that the hydroheat 25 can be circulated in the retort sterilization device 200. After the hydroheat 25 is transferred to the another tank, heat treatment with water steam may be performed by switching the openable/closable valves 31a through 31c, namely, by opening the openable/closable valve 31a and closing the openable/closable valves 31b and 31c.

According to the structure shown in FIG. 11, hydroheat may be circulated in the state where the liquid level of the hydroheat (warm water) 25 is higher than the top end of the liquid container 20 (liquid pot main body 21) and lower than the position of the product (heating object). In this case, the hydroheat can be released like a shower from the sparge pipes (hydroheat ejection sections) 52 to perform heating with the shower. In the case where the heating pot 50 of the retort sterilization device 200 in this embodiment is put into a pressurized state (by, for example, introducing compressed air), heating in a pressurized state can be performed.

Figure 12:
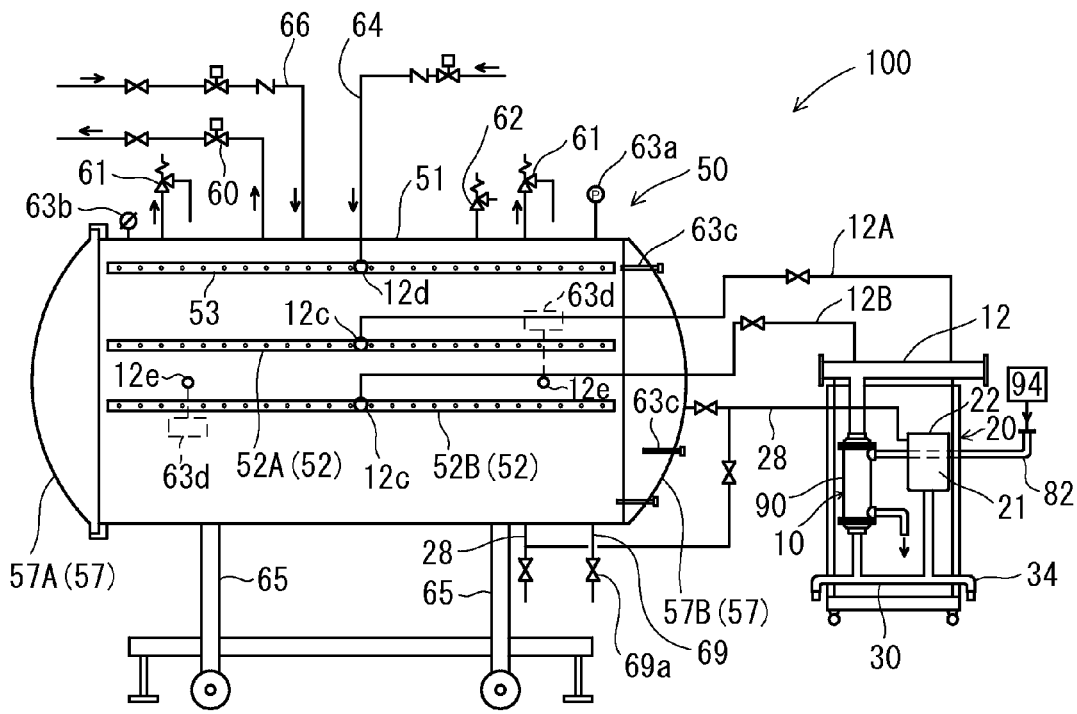
FIG. 12 is a schematic view showing a structure of a retort sterilization device (heating device) 100 in an embodiment according to the present invention.

In FIG. 5 and the like referred to above, the liquid container 20 (liquid pot main body 21) is located in the heating pot 50. Alternatively, as shown in FIG. 1, the liquid container 20 (liquid pot main body 21) may be located outside the heating pot 50. FIG. 12 is a structural view of the retort sterilization device 100 in which the liquid container 20 is located outside the heating pot 50.

In the retort sterilization device 100 shown in FIG. 12, a plurality of water steam ejection sections (sparge pipes) 52 (52A, 52B) are located in the heating pot 50. Also in the heating pot 50, a cooling water pipe (sparge pipe) 53 for ejecting cooling water is located. The cooling water pipe 53 is connected to a cooling water supply pipe (e.g., water pipe) 64 via through-holes 12d. The heating pot 50 is provided with the air discharge valve 60 for discharging air, the safety valves 61, a pressure adjustment valve (vacuum adjustment valve) 62 for adjusting the internal pressure of the heating pot 50, a pressure sensor 63a, a boost gauge 63b, temperature sensors 63c, core temperature sensors 63d and the like. Wiring lines for the core temperature sensors 63d are connected through throughholes 12e. On the lower part of the heating pot 50, the discharge pipe 69 is located. An air introduction pipe 66 for cooling air, introducing compressed air or the like is connected to the heating pot 50.

In the example shown in the figure, the pot main body 51 of the heating pot 50 is supported by the support rods (support table) 65. Wheels are attached to lower parts of the support rods 65. Therefore, the retort sterilization device 100 in this structural example can be moved to a desired position in a plant. As described above, minute-pressure vapor is introduced into the heating pot 50 by the water steam generation device 10 including the heat exchanger 90 and is circulated to raise the pressure and the temperature in a synchronous manner.

In the case where the liquid container 20 is provided outside the heating pot 50 as shown in FIG. 12, the existing heating pot 50 is usable, unlike in the case where the liquid container 20 is provided in the heating pot 50 as shown in FIG. 5. This provides an advantage that a heating pot of an existing retort sterilization device can be modified into the structure shown in FIG. 12. Since the existing heating pot is usable, there is an advantage that the production cost and facility cost can be suppressed. Even in the case where the liquid container 20 is provided outside the heating pot 50, the system of circulating warm water (hydroheat) as shown in FIG. 11 can be constructed by appropriately locating and connecting the pipes.

Figure 13:
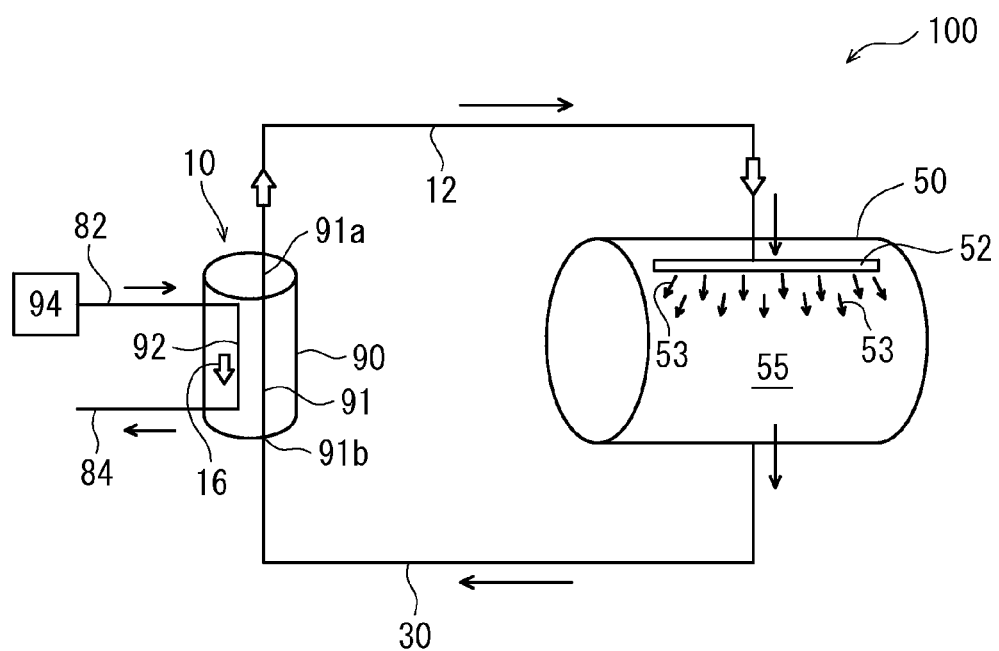
FIG. 13 is a schematic view showing a structure of a retort sterilization device (heating device) 100 in an embodiment according to the present invention.
Figure 14:
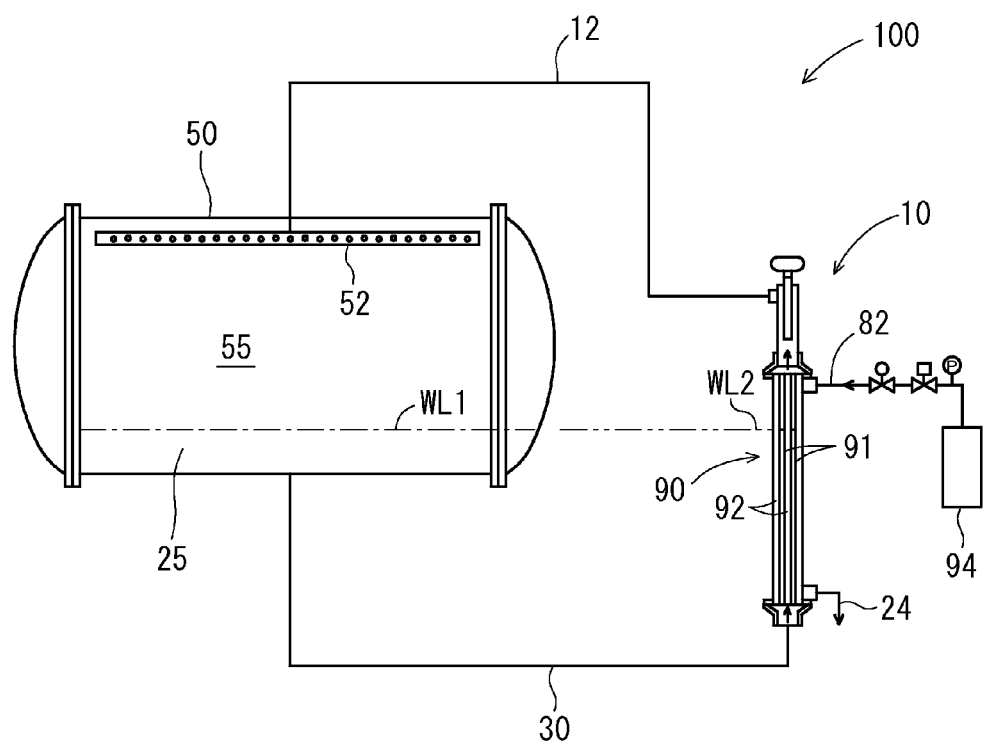
FIG. 14 is a schematic view showing a structure of a retort sterilization device (heating device) 100 in an embodiment according to the present invention.

In FIG. 1 and FIG. 12 described above, the liquid container 20 is provided outside the heating pot 50; and in FIG. 5 and the like, the liquid container 20 is provided in the heating pot 50. The method for raising the temperature and the pressure in the heating pot 50 using water steam is not limited to using the liquid container 20. For example, in FIG. 13, the communicating tube 30 is connected to the heating pot 50, and is also connected to the bottom end of the liquid path 91 of the heat exchanger 90. By this system also, the pressure and the temperature in the entire heating pot can be raised in a synchronous manner while water steam (minute-pressure vapor) is circulated. As shown in FIG. 14, the liquid 25 may be located in the bottom part in the heating pot 50 and thus stored, instead of using the liquid container 20. The systems shown in FIG. 13 and FIG. 14 are also usable for a heat treatment method using water steam, which includes the step of generating water steam by the water steam generation device 10 including the heat exchanger 90, the step of introducing water steam 53 into the heating pot 50, and the step of introducing the liquid 25 present in the bottom part in the heating pot 50 into the heat exchanger 90. In the step of heating by the heating pot 50, the water steam is circulated between the heat exchanger 90 and the heating pot 50, so that the internal area 55 of the heating pot 50 can be put into a pressurized state. The structure of the water steam ejection section 52, the discharge valves 60 (60a, 60b) and the like may be optionally modified in a preferable manner, as described above.

In the above-described embodiments, heat treatment of packaged food in a pressurized state (retort sterilization treatment) has been mainly described. The technique in this embodiment is not limited to this, and may be usable for heat treatment of food which is not packaged and/or heat treatment other than retort sterilization treatment. This will be described in more detail. When a conventional retort sterilization device is used for usual heat treatment of food, if boiler vapor is directly sprayed to food which is not retort-packaged (e.g., fish, meat, etc.), the food may be non-preferably burned or may caused to smell like a boiler by a component contained in the boiler vapor (alkaline component, etc.). In the system of spraying hydroheat at a high pressure, the food may be shredded due to the hydroheat, which is not preferable. By contrast, heating with water steam performed by the heating device (retort sterilization device) 100 in this embodiment is like a streaming step performed in a basket steamer, because water steam is saturated water vapor. Therefore, the food can be prevented from being dried during the heating and can be heated in a preferable manner. In the case where the gauge pressure of the water steam is 0 kg/cm$^2$, the amount of latent heat is 539.6 kcal/kg. The amount of latent heat of the water vapor is highest.

Food other than retort food can also be treated by the heating device 100 in this embodiment. Examples of the food which can be treated include frozen food (frozen fish, frozen meat, frozen vegetables, etc.), chilled food, seasoned food, dried food, and any other type of food suitable to the steaming step. Examples of the food which can be heated by the heating device 100 in this embodiment include rice, root crops, fish, meat (including processed food such as ham and the like), bread, tea, coffee, "tsukudani" (food boiled down in soy sauce, etc.) and the like. When frozen food or the like is heat-treated by the heating device 100 in this embodiment, drips are generated from the frozen food. According to the structure of this embodiment, the drips can be collected in the liquid container 20 used for generating water steam. In the case where the drips have an odor and it is desired to avoid the food from obtaining the odor, drips may be discharged through the drain pipe 34. Alternatively, the drips may be prevented from entering the liquid container 20 by the top lid 29. Still alternatively, the drips may be collected in an outer release pipe (another lower drain pipe) and discharged by an electric proportional valve or a manual valve.

Recently, fish which can be eaten down to bones is a target of attention. The heating device 100 in this embodiment performs heating with water steam, and therefore can easily produce a food product of such fish which can be eaten down to bones. For example, in the structure shown in FIG. 2, fish (e.g., frozen fish) 70 is put on the trays 72 and is heated. By adding water vapor to the food (fish), fish which can be eaten down to bones can be produced. The fish may be given a flavor with a seasoning or may be kneaded and minced. There is no specific limitation on the type of fish which can be heat-treated in this embodiment. Low-cost small fish is given a high added value. It has been confirmed that food heat-treated in this embodiment has very tasty. When fish having bones is heat-treated by the device in this embodiment, broiled fish which can be eaten down to bones can be provided. Examples of fish which can be heat-treated in this embodiment include blue-skinned fish such as mackerel, saurel, saury, sardine, and the like. These types of fish may have a thick fat layer between the epidermis and the fish meat. In addition, flatfish, flounder, cutlassfish, yellowtail, herring and the like (including whitemeat fish) may be used.

These types of fish can be used in the form of the entire body, in the state where a part of the body such as an internal organ, head or the like is removed, or in the state where the body is divided into parts. Parts with the bones, for example, the head, fins, backbone, little bones and the like are preferably usable. In the market, fish without bones is sold. However, it is costly to completely remove the bones of the fish. In consideration of the reuse of resources, the problem of garbage and the like, it is technologically highly valuable that the bones of the fish are softened so as to be eatable by the heat-treatment method or production method in this embodiment. This is also valuable in terms of nutrition because the bones of fish contain a lot of calcium. In addition, the softening of the bones solves the problem that senior citizens or children have a fishbone stuck in the throat.

The fish usable in this embodiment may be raw or pretreated. In this embodiment, "raw fish" encompasses fish which has not been heat-treated yet, for example, fish which is chilled, frozen, or partially frozen without being heat-treated. Pre-freezing fish and defrosted fish causes a problem in storage. Therefore, it is technologically significant that frozen fish can be put into the heating pot 50 in this embodiment in the frozen state and made eatable down to the bones.

The "pre-treated fish" usable in this embodiment refers to fish treated with any of various known methods performed on raw fish, except for heat-treatment. More specifically, "pre-treatment" encompasses various cooking methods and various processing methods performed on raw fish, and a part thereof. For example, "pre-treatment" encompasses impregnation treatment of impregnating with oil, extract, soup, salt, miso, soy sauce or the like; drying or dehydration treatment; fermentation treatment; treatment of attaching salt, pepper, flour, starch, rice flour, sesame, poppy seed, green laver, or powder or flake of any of other various types of food; treatment of providing any other food as filling; treatment of providing the brown color or cutting lines on the outer layer; and the like; and also a combination of two or more of these. In this specification, the "heat treatment" means treatment of denaturing protein in the fish by heat.

In the above, fish is described. Heat treatment by water steam can be made on meat (frozen meat, dried meat, processed meat such as ham and the like) and vegetables. A novel heating system (heat treatment with saturated water vapor), which cannot be performed by the conventional system of directly spraying boiler vapor or the conventional system of spraying hydroheat at a high pressure, can be carried out. Thus, a novel cooking method, a novel meal, and novel preserved food can be realized.

In the above embodiments, the liquid 25 has not been specifically described. The liquid 25 is typically water, and may be, for example, tap water, mineral water, ion exchange water, distilled water, or pure water. In addition, in the case where the food 70 is not packaged in a container, a seasoning may be added to the liquid 25, and the food may be heat-treated while being seasoned with water steam containing the seasoning.

In the structure in which the heating device 40 for heating water steam is provided in a part of the water steam supply pipes 12 (see FIG. 9), overheated vapor can be generated from the water steam. In the case where a plurality of heating devices 40 are directly coupled to each other, overheated vapor having a higher temperature can be generated.

Since the water steam generated by the heat exchanger 90 is saturated vapor (saturated water vapor), the overheated vapor introduced into the heating pot 50 is gas containing a large amount of moisture although having a high temperature. Therefore, the problem that when food is heated with overheated vapor generated as a result of heating water steam (saturated vapor), moisture is removed from the food more than necessary and the food becomes too dry can be suppressed. On this point, the overheated vapor generated by heating the water steam is different from the overheated vapor generated by heating high-temperature, high-pressure steam vapor to a high temperature (overheated vapor generated from steam vapor having a high degree of drying). This causes a difference in the quality (taste, dried state) of the resultant baked fish-processed product.

The overheated vapor has the following advantages. First, the overheated vapor has a feature of having a very high thermal efficiency because the overheated vapor is transmitted through convection and also through radiation. The baked state of fish or meat provided by the overheated vapor is equivalent to or higher than that provided by an open flame or gas. The overheated vapor is water vapor and thus is transmitted fast through convection, specifically by about 10 times faster than air. The overheated vapor has an original property of water vapor of being condensed when contacting a low-temperature substance and giving heat to the substance at the time of contact to raise the temperature (core temperature) of the substance, and also a property of heating a substance like heating air. Therefore, food can be baked within a short time. In addition, since the core temperature of a product is raised in a short time, the baking non-uniformity between the surface and the inside of the heating target (fish, meat, etc.) can be reduced.

The overheated vapor is in an oxygen-free state (or in a state of having a lower oxygen concentration than that of the atmosphere of the atmospheric pressure). Therefore, oxidation of fats and oils, destruction of vitamins and the like can be suppressed, and thus the preservation state of the product can be improved. In addition, the food is prevented from losing color. Water has a property of holding oil when being vaporized. This property is usable as a deoiling effect.

Cooking with overheated vapor having such characteristics does not remove too much moisture of the food, and thus can prevent the surface of the food from being hardened (e.g., production yield is 85% or higher) and bring out the taste of the food material. The overheated vapor is especially suitable for baking meat, a meat-processed product, or a fish-processed product. Specifically, when being baked with overheated vapor, meat, the meat-processed product, or the fish-processed product becomes more tasty and is softened. A reason for this is that since the meat, the meat-processed product, or fish is baked in a low oxygen state (or in a substantially oxygen-free state such that candlelight put into the heating pot 50 is extinguished), the fats and oils thereof are not oxidized and thus do not cause an uncomfortable odor of oil. Another reason is that since the temperature of the fish rises quickly, baking is performed in a preferable manner. In addition, in the case where the food contains a seasoning, the seasoning is entwined with the particles of gas or vapor and thus easily permeates into the fish meat. Thus, the fish becomes more tasty. In the heating pot 50, far infrared rays are generated because of the presence of the overheated vapor. This also improves the effect of heating. In the case where the temperature of the overheated vapor is 300° C. to 350° C. or greater, fish can be heated at a temperature far higher than 200° C., which is the boiling point of the fats and oils of the fish. This is also why the fish is tasty. Examples of the meat and the meat-processed product include beef, pork, chicken, mutton, ham, bacon and the like. The overheated vapor is not limited to being used for meat, fish and processed products thereof, and is also usable effectively for heating vegetables and for roasting tea or coffee beans.

For the heating pot 50 in this embodiment, a plurality of heating devices (electric heaters) 40 may be connected in series, so that overheated vapor having a temperature of, for example, 300° C. to 400° C. or higher (e.g., 550° C.) may be generated and introduced. In this case also, the retort sterilization device 100 can be operated while the internal pressure of the pipes is substantially the atmospheric pressure. Specifically, the retort sterilization device 100 can be operated at an internal pressure of merely 0.12 MPaA or less at most. When the overheated vapor is used, the heating treatment is preferably performed with the internal pressure of the heating pot 50 being kept at a minute pressure (0.13 MPaA to 0.15 MPaA) without being raised much, while the vapor is discharged from the lower part of the heating pot 50. In order to perform heating to a high temperature of 300° C. to 400° C. or higher using the boiler, an operation pressure of several atmospheric pressure or higher is needed, needless to say.

A reason why the heating device 40 can be operated at substantially 1 atmospheric pressure is that high-temperature overheated vapor can be generated by heating the water stream, which is minute-pressure vapor. In accordance with the technological common knowledge, in order to generate high-temperature gas, a high pressure is needed. However, when, for example, heat high-temperature, high-pressure boiler vapor is to be heated, it is actually difficult to heat the boiler vapor in a successful manner, or even if the boiler vapor is heated, an inefficiently huge amount of energy is required, because the flow rate of the boiler vapor is high. By contrast, according to the structure of this embodiment, water steam as the minute-pressure vapor drifts slowly in the pipe path. Therefore, during this time period, the food can be heated by the electric heater. Overheated vapor of a high temperature (e.g., 300° C. or higher) can be generated at substantially the atmospheric pressure. In the case where the retort sterilization device 100 is in a pressurized state, the overheated vapor is generated in the pressurized state.

The overheated vapor generated by the heating device 40 preferably has a temperature of 180° C. or higher. A reason for this is that the overheated vapor generated by heating water steam (saturated vapor) changes properties thereof at about 180° C. and becomes suitable for heat treatment performed on food materials or the like. This will be described in more detail. Overheated vapor generated by heating saturated vapor is very lightweight and easily fills an enclosed space down to corners thereof. The overheated vapor has a high rate of expansion, a low content of oxygen, and a high heat transmission rate. When a food material is heated using such overheated vapor, the surface layer of the food material can be burned. The overheated vapor permeates into the outer layer to raise the internal temperature thereof, and can vaporize only the moisture of the surface layer. As a result, the inside of the food material can be baked in a juicy state while the surface is browned to look delicious. The overheated vapor has a property of changing the temperature thereof rapidly by a small change of the amount of heat. Therefore, it is preferable for heat treatment of food that overheated vapor having a temperature of 180° C. or higher is generated and introduced into the internal area 55 of the heating pot 50, as opposed to relatively unstable overheated vapor of about 120° C.

Now, with reference to FIG. 15, a production device (production system) 300 of a fish-processed product including the heating device 100 in this embodiment, and a method for producing the fish-processed product will be described.

Figure 15:
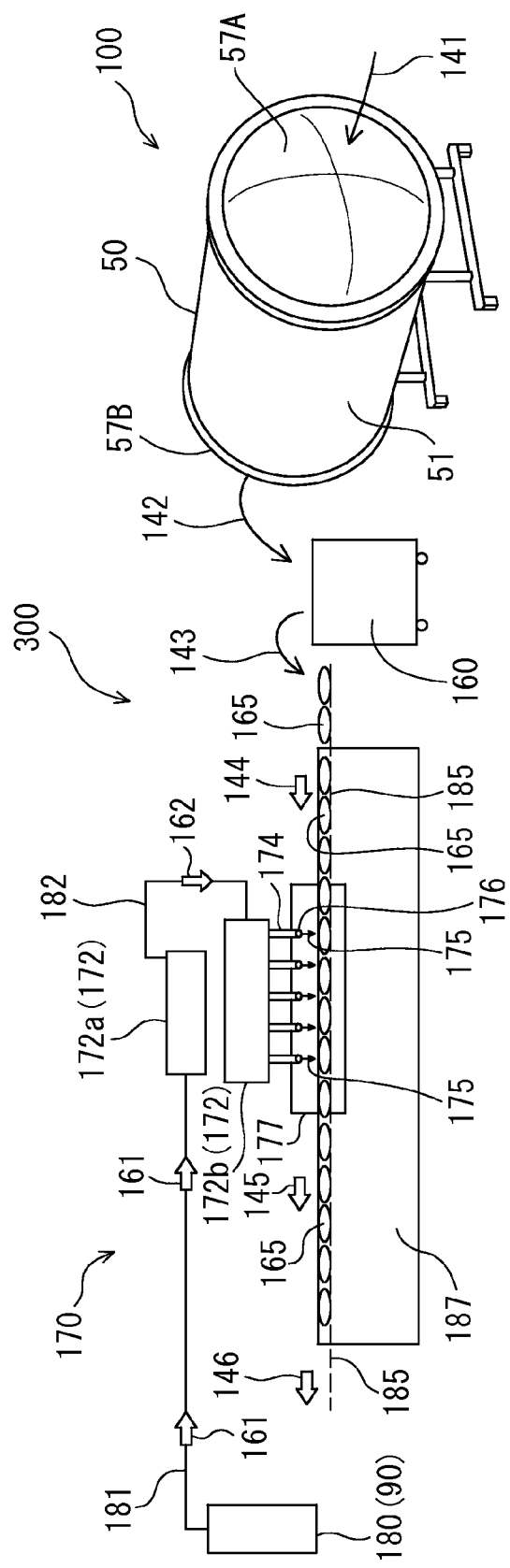
FIG. 15 shows a structure of a production system 300 of a fish-processed product in an embodiment according to the present invention.
Figure 16:
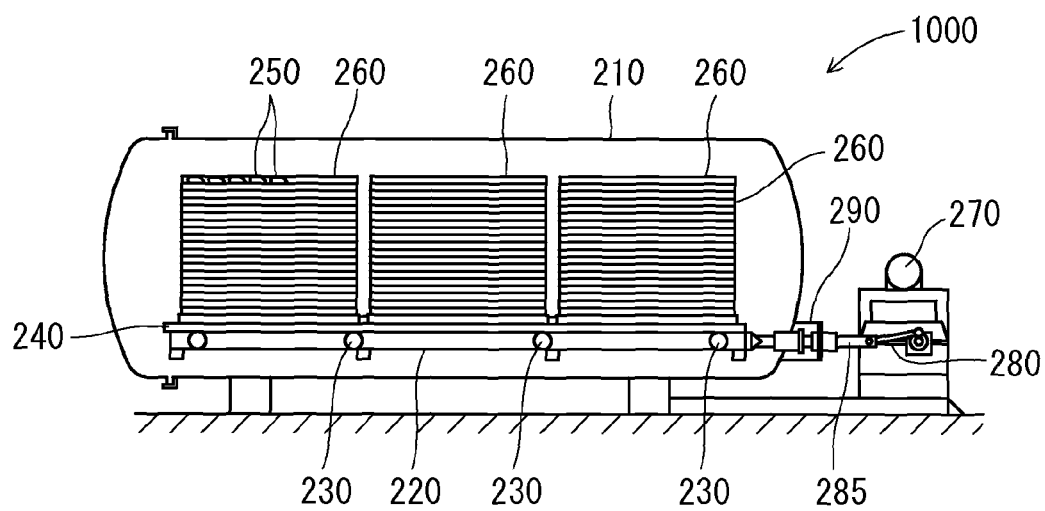
FIG. 16 is a cross-sectional view showing a structure of a conventional retort sterilization device 1000.

The production system 300 of a fish-processed product shown in FIG. 15 includes the heating device 100 including the above-described heating pot 50, a kneader 160 for kneading fish heated by the heating pot 50, and a high-temperature vapor baking machine 170 for baking the kneaded fish.

The heating pot 50 shown in FIG. 15 includes a cylindrical (or generally cylindrical) main body 51. The heating pot 50 in this example has openable/closable doors 57A and 57B respectively at a front opening and a rear opening of the pot main body 51. Therefore, referring to FIG. 15, the door 57A at the front opening is opened to put the fish into the heating pot 50 as represented by arrow 141 to perform the heating step, and after the heating step, the door 57B at the rear opening is opened to take out the heated fish as represented by arrow 142. The heating pot 50 having the openable/closable doors 57A and 57B respectively at the front side and the rear side can improve the work efficiency of the production line. Needless to say, the heating pot 50 may have one openable/closable door (e.g., door 57A) through which fish is put into, and taken out of, the heating pot 50.

In this example, in a lower part in the heating pot 50, a plate (flat plate) may be provided. On the plate, for example, a basket steamer (formed of a metal or plastic material; not shown) packed with a plurality of pieces of frozen fish (frozen saurel) is placed. A plurality of basket steamers may be stacked on the plate. Alternatively, a plurality of basket steamers may be placed on the plate in parallel. Instead of the plate, a palette may be provided in the lower part in the heating pot 50. Below the plate, there is a opening for connecting the heating pot 50 and the communicating tube 30 directly or indirectly.

In this embodiment, a palette is packed with fish in a frozen state (e.g., frozen saurel) and is put into the heating pot 50 as represented by arrow 141 in FIG. 15. Then, the heating pot 50 of the heating device 100 in this embodiment is heated for about 1 hour to soften the bones. Next, as represented by arrow 142, the door 57B is opened and the heated palette is taken out, and then the heated fish is put into the kneader 160. In the kneader 160, the fish meat is kneaded with the softened bones to provide minced fish. During (or before or after) the kneading step performed by the kneader 160, a seasoning (e.g., vegetable oil, amino acid, salt, etc.) is added to, and mixed with, the minced fish. The pre-treatment described above may be performed on this stage.

Next, the fish (fish-processed product) kneaded and then flaked is baked by the high-temperature vapor baking machine 170. The high-temperature vapor baking machine 170 shown in FIG. 15 is a device for heating vapor (water vapor) to generate overheated vapor and baking a heating target (kneaded fish) 165 with the overheated vapor. As described above, the overheated vapor is vapor obtained by heating water vapor to a temperature exceeding 100° C. at a constant pressure. Unlike the water vapor or high-pressure, high-temperature water vapor, the overheated water vapor (or overheated vapor) is heat radiating gas for radiating far infrared rays suitable to heat food, and an atmosphere thereof has an advantage of, for example, blocking oxygen and thus preventing oxidation. It is known that when overheated water vapor is used, fish, meat and the like can be, for example, baked to be tasty.

A high-temperature vapor baking machine using overheated vapor typically heats high-temperature, high-pressure boiler vapor by a baking device including a burner which provides a larger amount of heat (or a high-output electromagnetic heating device) to generate overheated vapor, and uses the overheated vapor. However, such a machine does not have a high energy efficiency. The high-temperature vapor baking machine 170 in this embodiment heats water steam (minute-pressure vapor) by a heating device (e.g., electric heater) to generate overheated vapor, and sprays the overheated vapor to the heating target (kneaded fish) 165 to bake the kneaded fish 165.

The high-temperature vapor baking machine 170 shown in FIG. 15 will be described more specifically. The high-temperature vapor baking machine 170 includes a water steam generation device 180 for generating water steam 161, and a heating device 172 for heating the water steam 161 to generate overheated vapor 162 (or 175). The generated overheated vapor 162 is introduced into a baking chamber 177 for baking the kneaded fish 165. In the baking chamber 177, ejection pipes 174 for ejecting the overheated vapor 175 are located.

The heating device 172 in this embodiment is, for example, an electric heater. In the example shown in FIG. 15, a plurality of heating devices 172a and 172b are connected in series. One heating device 172 may be provided, or three or more heating devices may be connected in series. The heating devices 172 may be located in parallel, instead of in series, so that the overheated vapor 162 and 175 can be generated from the water steam 161. The water steam generation device 180 for generating the water steam 161 is connected to the heating device 172 (172a) via a water steam supply pipe 181. The heating device 172 (first heating section 172a) is connected to the heating device 172 (second heating section 172b) via a vapor pipe 182. The second heating section 172b is connected to the ejection pipes 174. The ejection pipes 174 each have an ejection opening 176 at a tip thereof, through which the overheated vapor 175 is ejected.

The high-temperature vapor baking machine 170 in this embodiment includes a belt conveyor 185 passing through the baking chamber 177. The baking chamber 177 is an open space which is opened at an entrance and an exit for the belt conveyor 185. The ejection openings 176 of the ejection pipes 174 are located above the belt conveyor 185. The baking chamber 177 is formed of, for example, stainless steel. In this embodiment, the ejection pipes 174, the vapor pipe 182, and the water steam supply pipe 181 are also formed of stainless steel.

In this embodiment, the fish 165 kneaded by the kneader 160 is put on the belt conveyor 185 as represented by arrow 143. The belt conveyor 185 advances as represented by arrow 144, and the kneaded fish 165 is baked in the baking chamber 177 with the overheated vapor 175. Then, along with the movement of the belt conveyor 185 represented by arrow 145, the baked fish 165 comes out of the baking chamber 177 and flows downstream as a baked product (fish-processed product). In the example shown here, the kneaded fish 165 is put on a metal (e.g., stainless steel) net in a thin, spread state. The net having the thin, spread fish 165 is put on the belt conveyor 185, and the fish 165 is baked with the overheated vapor 175.

According to the production method in this embodiment, fish heated by the heating pot 50 (fish softened to the bones) is kneaded, so that even bones, head and fins are eatable without being disposed of. In the case where a seasoning is added during the kneading, adjustment of taste can be omitted in a step thereafter (baking step) and thus the work of producing the fish-processed product flows well. The kneaded fish is put on the belt conveyor 185 as being spread to be thin (e.g., to a thickness of about 1 cm to 5 cm) and thus can be baked with the overheated vapor efficiently (since the fish is thin, heat is transmitted well and the fish can be baked uniformly). Instead of being spread to be thin, the fish may be put into balls or blocks before being baked.

According to the high-temperature vapor baking machine 170 in this embodiment, water steam as minute-pressure vapor drifts slowly in the heating device (electric heater) 172. Such water steam can be heated efficiently by the electric heater 172 as compared with high-pressure vapor transferring at a high rate. As a result, the overheated vapor 175 having a high temperature (e.g., 300° C. or higher) can be generated at the atmospheric pressure. The high-temperature overheated vapor 175 can be sprayed, while having the high-temperature, to the fish (heating target) 165 on the belt conveyor 185 located right below. The heating device 172 in this embodiment is, for example, an electric heater, and can perform heating at substantially the same internal pressure as the atmospheric pressure (e.g., internal pressure of 1.2 atmospheric pressure or less) during operation.

As the water steam generation device 180 shown in FIG. 15, any device for generating water steam is usable with no specific limitation. It is preferable that the water steam generation device 180 includes the above-described heat exchanger 90 from the viewpoints of energy efficiency and continuous use. When, for example, the temperature of the water steam generated by the water steam generation device 180 is about 95° C. to 110° C., the water steam is generated by the electric heaters 172 (172a, 172b) to become overheated vapor (superheated vapor) having a temperature of 150° C. or higher, preferably 180° C. or higher (or 300° C. to 600° C. or higher). The electric heater 172 in this embodiment is, for example, of about several kilowatts (e.g., plug heater, flange heater, etc.).

Since the water steam 161 is saturated vapor (saturated water vapor), the overheated vapor introduced into the baking chamber 177 is gas containing a large amount of moisture although having a high temperature. Therefore, the problem that when food is heated with overheated vapor generated as a result of heating water steam (saturated vapor), moisture is removed from the food more than necessary and the food becomes too dry can be suppressed. On this point, the overheated vapor generated by heating the water steam is different from the overheated vapor generated by heating high-temperature, high-pressure steam vapor to a high temperature (overheated vapor generated from steam vapor). This causes a difference in the quality (taste, dried state) of the resultant baked fish-processed product.

The high-temperature vapor baking machine 170 in this embodiment can generate overheated vapor having a temperature of, for example, 300° C. to 400° C. or higher (e.g., 550° C.), but is operated at an internal pressure of substantially 1 atmospheric pressure. Specifically, the high-temperature vapor baking machine 170 is operated at 1.2 atmospheric pressure or less at most. In order to perform heating to a high temperature of 300° C. to 400° C. or higher using the boiler, an operation pressure of several atmospheric pressure or higher is needed, needless to say.

A reason why the high-temperature vapor baking machine 170 can be operated at substantially 1 atmospheric pressure is that high-temperature overheated vapor can be generated by heating the water stream, which is minute-pressure vapor. In accordance with the technological common knowledge, in order to generate high-temperature gas, a high pressure is needed. However, when, for example, high-temperature, high-pressure boiler vapor is to be heated, it is actually difficult to heat the boiler vapor in a successful manner, or even if the boiler vapor is heated, an inefficiently huge amount of energy is required, because the flow rate of the boiler vapor is high. By contrast, according to the structure of this embodiment, water steam as the minute-pressure vapor drifts slowly in the pipe path. Therefore, during this time period, the food can be heated by the electric heater. Overheated vapor of a high temperature (e.g., 300° C. or higher) can be generated at the atmospheric pressure.

According to the high-temperature vapor baking machine 170 in this embodiment, even though the baking chamber 177 is of an open type, frozen fish (frozen mackerel, etc.), for example, can be completely defrosted and also baked within several minutes when the temperature of the overheated vapor is set to 300° to 400° C. (in a typical example, 400° C.±10° C.) or 300° C. to 550° (in a typical example, 450° C±10° C.). Therefore, the fish 165 which has been heated and kneaded can be baked successfully with the overheated vapor 175.

It is preferable that the temperature of the overheated vapor 175 ejected from the ejection pipes 174 is 180° C. or higher. A reason for this is that the overheated vapor generated by heating water steam (saturated vapor) changes properties thereof at about 180° C. and becomes suitable for heat treatment performed on food materials or the like. This will be described in more detail. Overheated vapor generated by heating saturated vapor is very lightweight and easily fills an enclosed space down to corners thereof. The overheated vapor has a high rate of expansion, a low content of oxygen, and a high heat transmission rate. When a food material is heated using such overheated vapor, the surface layer of the food material can be burned. The overheated vapor permeates into the outer layer to raise the internal temperature thereof, and can vaporize only the moisture of the surface layer in a large amount. As a result, the inside of the food material can be baked in a juicy state while the surface is browned to look delicious. The overheated vapor has a property of changing the temperature thereof rapidly by a small change of the amount of heat. Therefore, it is preferable for heat treatment of food that overheated vapor having a temperature of 180° C. or higher is generated and introduced into the baking chamber 177, as opposed to relatively unstable overheated vapor of about 120° C.

In the example shown in FIG. 15, the ejection pipes 174 are inserted from above the baking chamber 177. The ejection pipes 174 are not limited to this. For example, the ejection pipes 174 may be introduced from the side of the baking chamber 177 (left side, right side, or both of the left side and the right side) such that the ejection openings 176 of the ejection pipes 174 are located above the belt conveyor 185. There is no specific limitation on the number or positions of the ejection pipes 174, which may be appropriately selected in accordance with the baking conditions. The ejection pipes 174 and the ejection openings 176 thereof may be located above and below the belt conveyor 185, so that the food is baked from both sides. The distance between the ejection pipes 174 and the heating device (electric heater) 172 closest to the ejection pipes 174 may be short. In this case, the overheated vapor 175 can be sprayed to the fish (food) 165 while the temperature of the overheated vapor 175 is prevented from decreasing.

The fish-processed product in this embodiment is usable in a wide range including ingredients of rice balls, ingredients of sandwiches, ingredients of fish-mixed rice, toppings of salad, ingredients of pasta and the like. When fish is eaten with bones, the calcium intake is ten times higher than that when fish without bones is eaten. Therefore, fish with bones is optimal as health food. The fish may be provided in the state where the entire body including bones is treated, or as an IQF (Individual Quick Frozen) product with the bones being soften while the shape of the fish being kept. In the latter case, the product can be eaten with a taste of boiled fish. Slices of fish may be provided as tempura. Tempura may be cooked by the high-temperature vapor baking machine 170 with the overheated vapor after oil is applied to the surface of the fish, instead of being deep-fried with oil. A fish-processed product can be provided with the shape of broiled fish or boiled fish being left. For providing a fish-processed product with the shape of fish being left, the fish is merely heated by the heating pot 50 of the heating device 100 (or, additionally baked by the high-temperature vapor baking machine 170) without being kneaded by the kneader 160.

The production method of a fish-processed product in this embodiment according to the present invention includes the step of heating fish having bones by the heating pot 50. In this embodiment, the production method further includes the step of kneading the fish heated by the heating pot 50, and the step of baking the kneaded fish by the high-temperature vapor baking machine 170. In the step of heating, the top end 91a and the bottom end 91b of the liquid path 91 of the heat exchanger 90 are connected to the heating pot 50 via the pipes 12 and 14 respectively, and the water steam 15 is circulated between the heat exchanger 90 and the heating pot 50, so that the internal area 55 of the heating pot 50 is put into a pressurized state. Therefore, by continuously introducing the water steam into the heating pot 50 while circulating the water steam between the heat exchanger 90 and the heating pot 50, the fish located in the heating pot 50 can be heated while being gradually pressurized. As a result, in the heating step, the bones of the fish can be softened.

According to International Publication WO2006/025102 proposing a production method of a fish-processed product which is softened down to the bones, the step of decreasing the pressure is necessary. With the heating device 100 in this embodiment, such a step decreasing the pressure is not necessary, and thus significant energy loss can be suppressed. In the step of heating in a pressurized state, air for pressurization does not need to be introduced, and the step of heating can be performed by a heating pot which can be pressurized efficiently. In the step of heating, boiler vapor does not enter the heating pot. This provides advantages that there is no boiler vapor odor in the heating pot and the retort pouch does not smell like boiler vapor.

Since the fish (fish meat) with softened bones is kneaded and baked by the high-temperature vapor baking machine 170, the bones, fins, head and the like of the fish can be used without being disposed of. As described above, the calcium intake provided by a fish food product in which bones are eatable is about ten times higher than that provided by a fish food product with no bones. Thus, the technique in this embodiment decreases the amount of wastes and thus decreases the material cost, which is preferable environmentally. The technique of this embodiment is also preferable for health in terms of calcium intake. Since the kneaded fish is baked by the high-temperature vapor baking machine 170, the fish is more tasty. The high-temperature vapor baking machine 170 bakes in an oxygen-free state (e.g., at a temperature of 300° C. or higher). Therefore, the fat components of the fish baked by this machine is not oxidized and thus the fish does not have a fat odor, as opposed to the fish baked by a burner. Baking by the high-temperature vapor baking machine 170 also provides effects that the temperature of the fish is raised quickly and that a seasoning is entwined with particles of gas or vapor and thus easily permeates into the fish meat to make the fish more tasty.

The heat treatment performed by the heating pot 50 of the heating device 100 is suitable for fish having bones. Needless to say, a processed marine product (and/or food product) with no bones can be heated by the heating pot 50 of the heating device 100. The heat treatment method performed by the heating pot 50 is usable for any type of food, not only for fish, as a simple heat treatment method performed in a pressurized state. As described above, the range of uses of the heating device 100 (or the heating pot 50) in this embodiment is wide. Monitoring was conducted for obtaining general evaluation on products (fish-processed products) in this embodiment. Ten out of ten people evaluated the products very highly, and thus the tastiness of the products has been proved.

So far, preferable embodiments of the present invention have been described. The present invention is not limited to these embodiment, and can be modified in various manners, needless to say. The features of the devices shown in the figures can be combined appropriately, and each figure does not disclose only the structure of the device shown therein. For example, the water steam ejection section 52 located in an upper part in the device shown in FIG. 14 is usable to a device shown in another figure. The device shown in FIG. 14 may have the air discharge pipe 60 or the like.

According to the present invention, a retort sterilization device and a heating device having a high energy efficiency and/or capable of suppressing heating non-uniformity can be provided.

Description Of Reference Characters
10 Water steam generation device
12 Water steam supply pipe
15 Water steam
18 High-temperature hydroheat
20 Liquid container
21 Liquid pot main body
21a Top opening (opening)
22 Lid
23 Water level adjustment member
25 Liquid
26 Pipe (water pipe)
28 Coupling pipe
29 Top lid
30 Communicating tube
31a, 31b, 31c Openable/closable valve
32a First path
32b Second path
33 Openable/closable valve
34 Drain pipe
35 Circulation pump
40 Heating device (electric heater)
50 Heating pot
51 Pot main body
51a Securing member
52 Water steam ejection section (sparge pipe)
55 Internal area of the heating pot
57 Door
58 Hinge
59 Lever
60 Air discharge valve
61 Safety valve
62 Vacuum adjustment valve
63 (63a-63d) Sensor
65 Support rod
66 Air introduction pipe
67 Base
69 Discharge pipe
70 Heating target (retort food)
72 Container (tray)
75 Plate
82 Boiler pipe
84 Exhaust steam pipe
90 Heat exchanger
91 Liquid path
92 Vapor path
93 Outer casing
94 Boiler
100 Retort sterilization device (heating device)
160 Kneader
161 Water steam
162 Overheated vapor
165 Heating target (kneaded fish)
170 High-temperature vapor baking machine
172 Heating device (electric heater)
174 Ejection pipe
175 Overheated vapor
176 Ejection opening
177 Baking chamber
180 Water steam generation device
181 Water steam supply pipe
182 Vapor pipe
185 Belt conveyor
200 Retort sterilization device
220 Rail
230 Wheel
240 Movable table
250 Retort food
260 Tray
270 Motor
280 Crank mechanism
285 Driving shaft
290 Shaft sealing device
300 Production device (production system)
1000 Retort sterilization device

What is claimed is:

1. A retort sterilization device for performing heat sterilization in a pressurized state, comprising:

a heating pot for accommodating retort food; and
a water steam generation device for generating water steam which is minute-pressure vapor;
wherein:
the heating pot is connected to the water steam generation device;
the water steam generation device has a liquid path and a vapor path independent from each other, and includes a heat exchanger for performing heat exchange between liquid flowing in the liquid path and heating vapor flowing in the vapor path;
the heating vapor from a boiler is introduced into the vapor path of the heat exchanger;
a top end of the liquid path of the heat exchanger is connected via a water steam supply pipe to a water steam ejection section located in the heating pot;
the heat exchanger is connected to the liquid container for storing the liquid to be supplied to the heat exchanger;
a bottom end of the liquid path of the heat exchanger is connected to the liquid container via a communicating tube;
the liquid container is coupled to the heating pot; and
the heat exchanger, the liquid container, and the heating pot are connected so as to form a sealed space.

2. The retort sterilization device of claim 1, wherein:
the liquid is stored in the liquid container; and
a water level of the liquid in the liquid container matches a water level of the liquid in the liquid path of the heat exchanger.

3. The retort sterilization device of claim 1, wherein the liquid container is provided with a water level adjustment member for adjusting the water level of the liquid.

4. The retort sterilization device of claim 1, wherein the liquid container is connected to the heating pot via a coupling pipe.

5. The retort sterilization device of claim 4, wherein:
the liquid container includes a liquid pot main body having a top opening in an upper part thereof and a lid for sealing the top opening of the liquid pot main body;
the liquid pot main body is a pressure-resistant container;
a bottom part of the liquid pot main body is connected to the communicating tube; and
the lid is connected to the coupling pipe.

6. The retort sterilization device of claim 1, wherein:
the liquid container includes a liquid pot main body having a top opening in an upper part thereof; and
the liquid pot main body is attached to the heating pot such that the top opening is located in the heating pot.

7. The retort sterilization device of claim 6, wherein a bottom surface of the liquid pot main body is connected to the communicating tube.

8. The retort sterilization device of claim 6, wherein a top lid which does not seal the top opening is provided at the top opening of the liquid pot main body.

9. The retort sterilization device of claim 1, wherein:
the heating pot is cylindrical; and
a plate on which a container for accommodating the retort food is to be placed is located in the heating pot.

10. The retort sterilization device of claim 1, wherein the water steam ejection section is a sparge pipe located so as to extend in a horizontal direction in the heating pot.

11. The retort sterilization device of claim 1, wherein a plurality of the water steam ejection sections are located in the heating pot.

12. The retort sterilization device of claim 1, wherein the water steam ejection section is located in a lower area in the heating pot.

13. The retort sterilization device of claim 12, wherein:
at least two of the water steam ejection sections are located in the lower area in the heating pot; and
at least two of the water steam ejection sections are located in an area above the lower area in the heating pot.

14. The retort sterilization device of claim 1, wherein a lower part of the heating pot is connected to a discharge pipe for discharging gas in the heating pot to outside the heating pot.

15. The retort sterilization device of claim 14, wherein:
the discharge pipe is connected to a variable valve for varying an opened/closed state of the discharge pipe; and
the discharge pipe is capable of discharging drip water from a bottom part of the heating pot.

16. The retort sterilization device of claim 1, wherein the heating pot is provided with at least one of an air discharge valve for discharging air in the heating pot to outside the heating pot and a proportional valve as a pressure relief valve for adjusting an internal pressure.

17. The retort sterilization device of claim 16, wherein the air discharge valve is attached to a highest part of the heating pot.

18. The retort sterilization device of claim 1, wherein a heating device for heating the water steam is provided at a part of the water steam supply pipe connected to the water steam ejection section.

19. The retort sterilization device of claim 18, wherein the heating device is an electric heater.

20. The retort sterilization device of claim 1, wherein the retort sterilization device is a pressurization and heating device for circulating the water steam through the heat exchanger, the heating pot and the liquid container to put an internal area of the heating pot into a pressurized state.

21. The retort sterilization device of claim 1, wherein the water steam generated by the water steam generation device is saturated water vapor having a minute pressure of 0.12 MPaA or less.

22. The retort sterilization device of claim 1, wherein a cooling water supply pipe is connected to a part of the water steam supply pipe such that cooling water is ejected from the water steam ejection section.

23. The retort sterilization device of claim 1, wherein the communicating tube for providing communication between the heat exchanger and the liquid container is branched into a first path and a second path.

24. The retort sterilization device of claim 23, wherein a circulation pump for circulating the liquid is located in the second path.

* * * * *